United States Patent [19]
Han et al.

[11] Patent Number: 5,891,864
[45] Date of Patent: Apr. 6, 1999

[54] ANTI-CANCER COMPOSITIONS

[75] Inventors: Yung Bok Han, 226-5, Jeongreung-dong, Seongbuk-gu, Seoul; Hong Ki Kyung, Sungnam; Chun Won Kim, Seoul; E Tay Ahn, Seoul; Jong Bae Kim, Pohang; Hyo Suk Lee, Seoul; Kyung Yung Lee, Seoul; Eun Kyung Hong, Kunpo; Hee Sook Choi, Seoul; Sang Geon Kim, Seoul; Bo Im Yoo, Seoul; Hae Kyung Kwon, Seoul, all of Rep. of Korea

[73] Assignees: Yung Bok Han, Seoul; Tae Rim Pharm. Co., Ltd., Kyungki-do, both of Rep. of Korea

[21] Appl. No.: 552,615

[22] Filed: Nov. 3, 1995

[30]     Foreign Application Priority Data

May 24, 1995 [KR] Rep. of Korea ...................... 95-13068

[51] Int. Cl.$^6$ ........................... A61K 31/70; A61K 31/44
[52] U.S. Cl. ............................ 514/45; 514/297
[58] Field of Search ........................................ 514/45, 297

[56]             References Cited

PUBLICATIONS

Iigo et al., J. Pharmacobio–Dyn 5(7) 1982 pp. 515–520 (The original veterence to follow in due course).
Dyer, An index of Tumor Chemotherapy, (1949), with, pp. 10–12 and 130 ( No. 3750–3757).

*Primary Examiner*—Jerome D. Goldberg
*Attorney, Agent, or Firm*—Birch, Stewart, Kolasch & Birch, LLP

[57]             ABSTRACT

The present invention relates to an anti-cancer composition containing acridine derivatives and guanosine compounds. In the composition of the present invention, the acridine derivative and the guanosine compound are present in the weight ratio of 1:0.1–5.0, preferably 1:0.3–3.0 and more preferably 1:0.5–1.5. In the composition of the present invention, most preferably the acridine derivative is acriflavine neutral and the guanosine compound is guanosine hydrate. Although acridine derivatives and guanosine compounds used as an active ingredient in the present composition have substantially no anti-cancer effect when they are used individually, the combination of acriflavine neutral and guanosine hydrate which potentiates the effect of acriflavine neutral, i.e. the composition(AG60) according to the present invention, exhibits reduced toxicity and increased anti-cancer effect in comparison to the use of acriflavine neutral or guanosine hydrate alone.

11 Claims, 25 Drawing Sheets
(18 of 25 Drawing Sheet(s) Filed in Color)

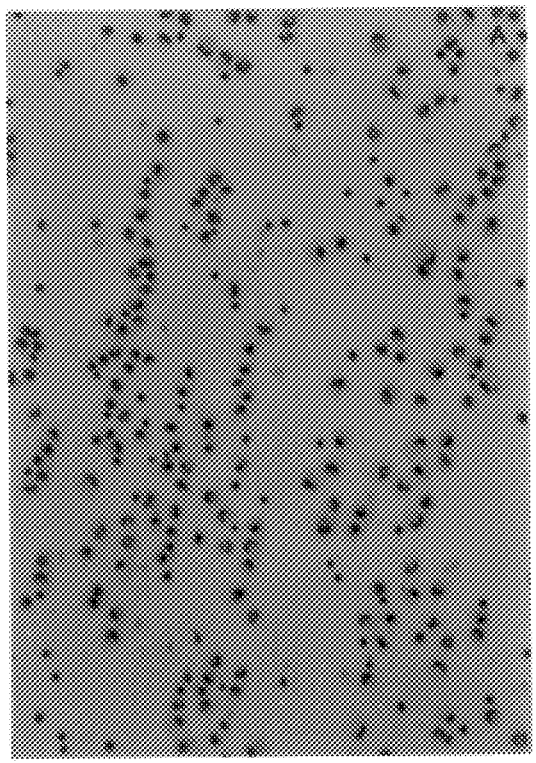
FIG. 8A
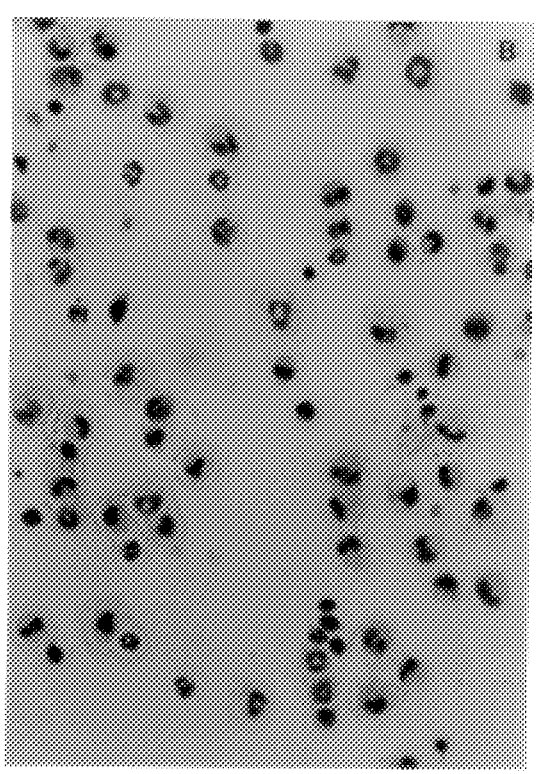
FIG. 8B
FIG. 8C
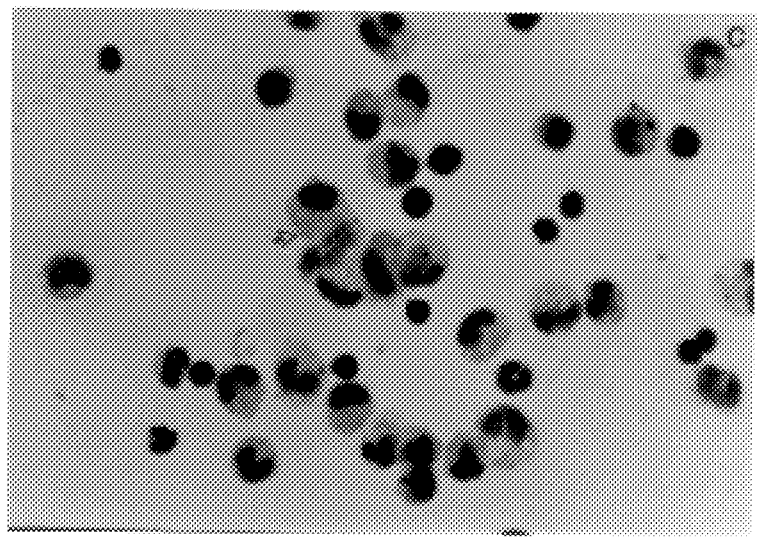

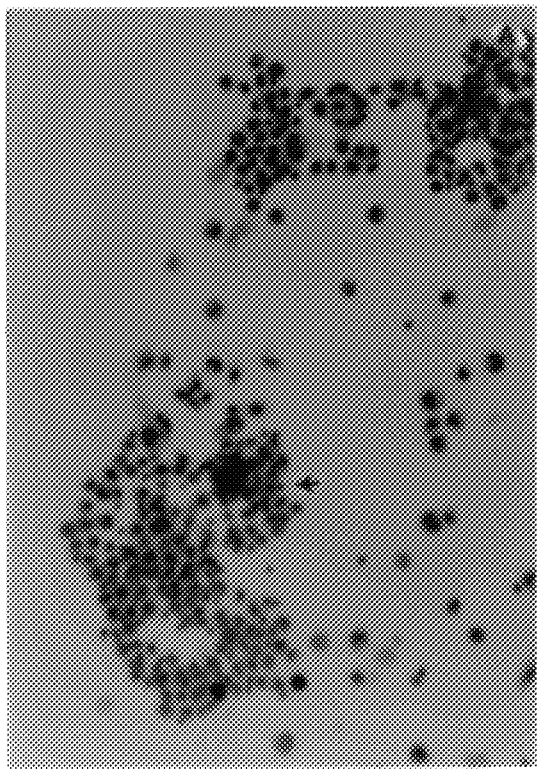
FIG. 10A
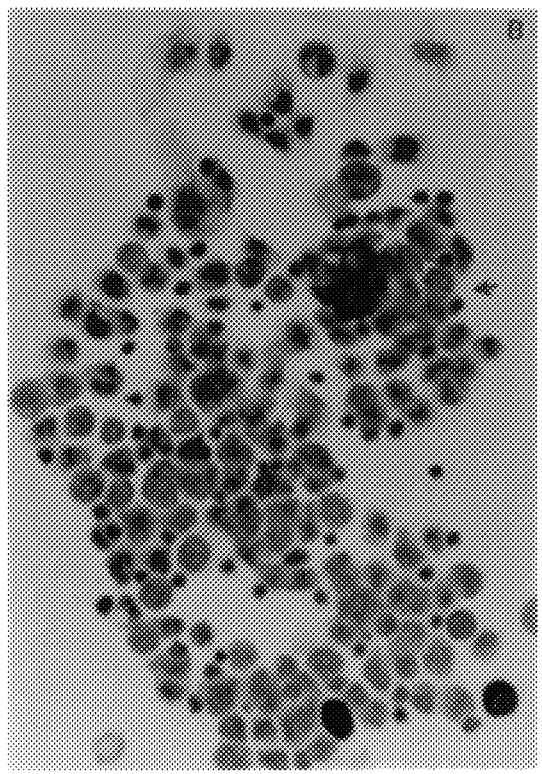
FIG. 10B
FIG. 10C
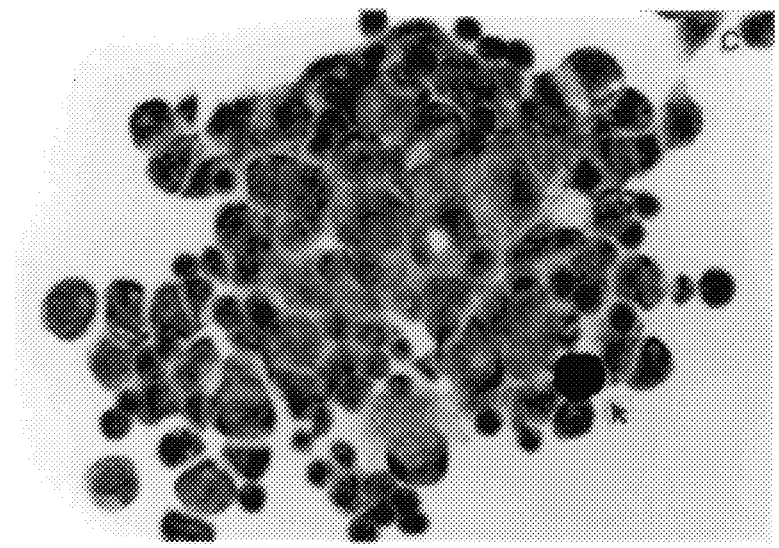

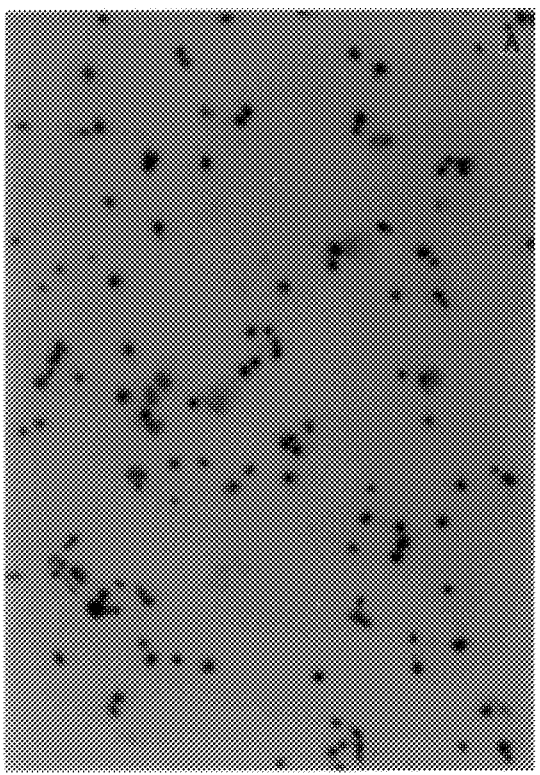
FIG. 11A
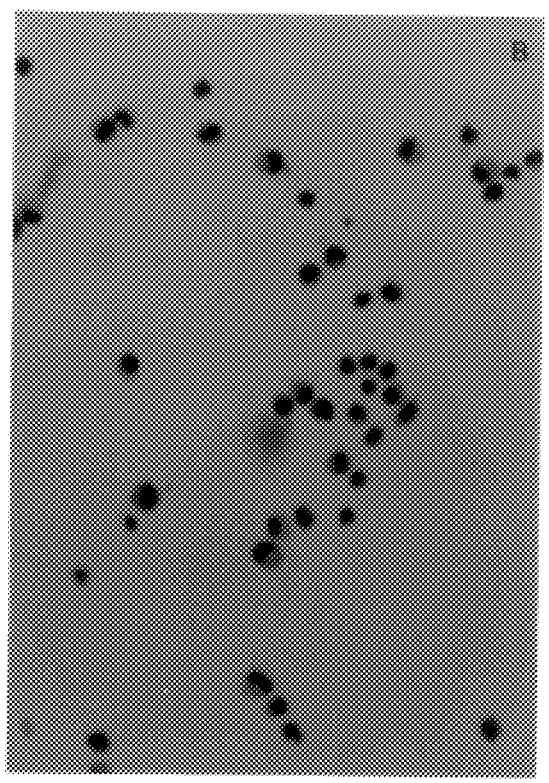
FIG. 11B
FIG. 11C
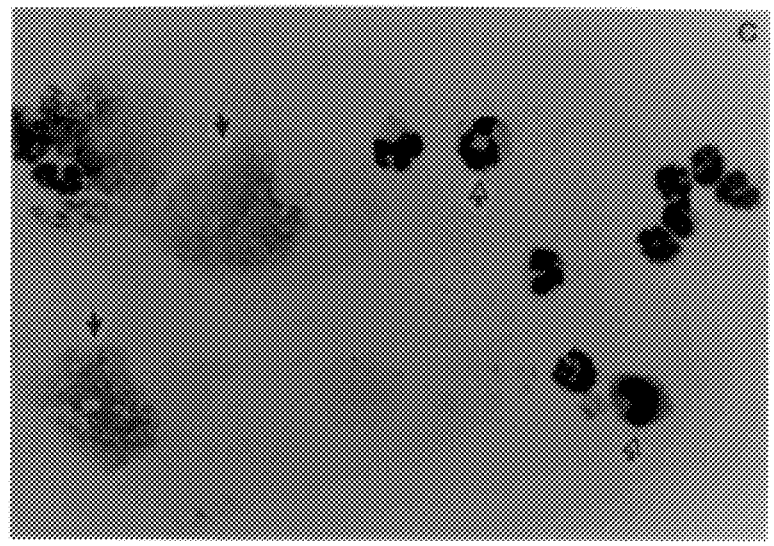

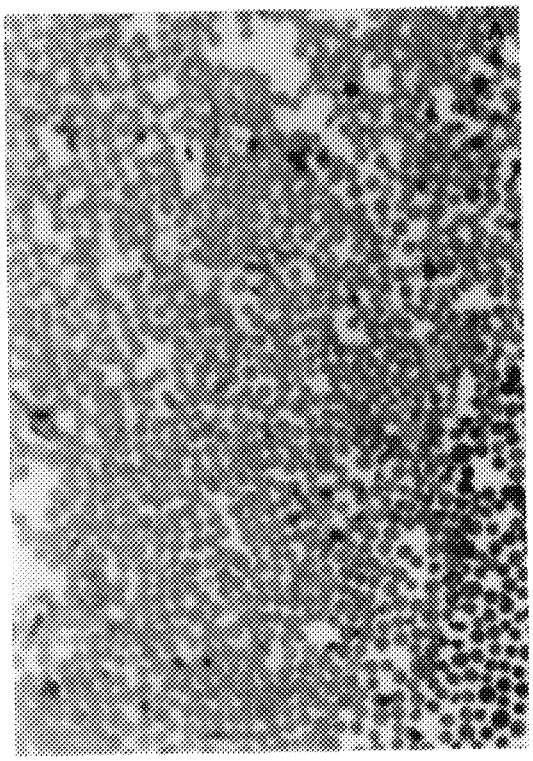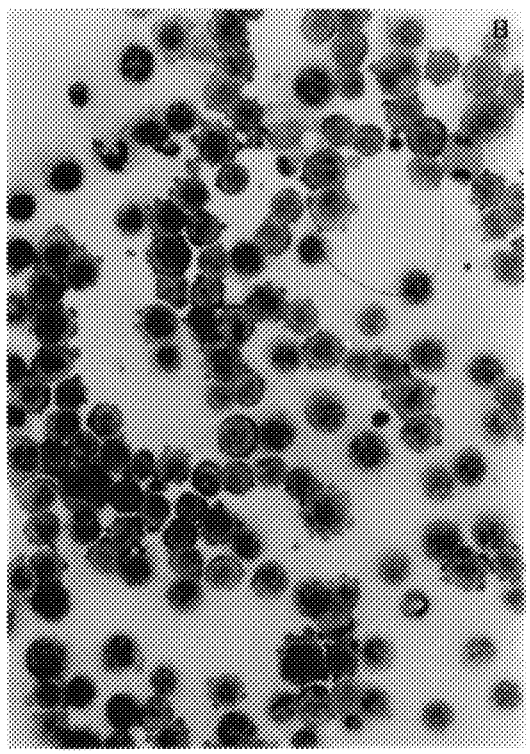
FIG. 13A    FIG. 13B
FIG. 13C
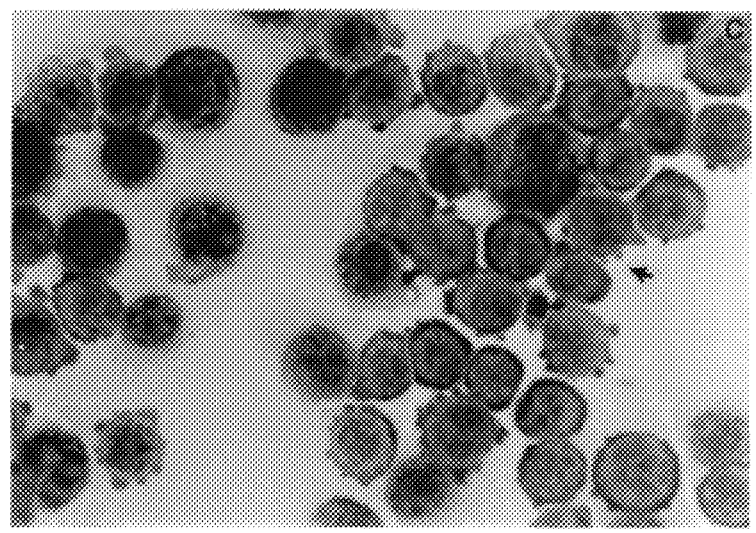

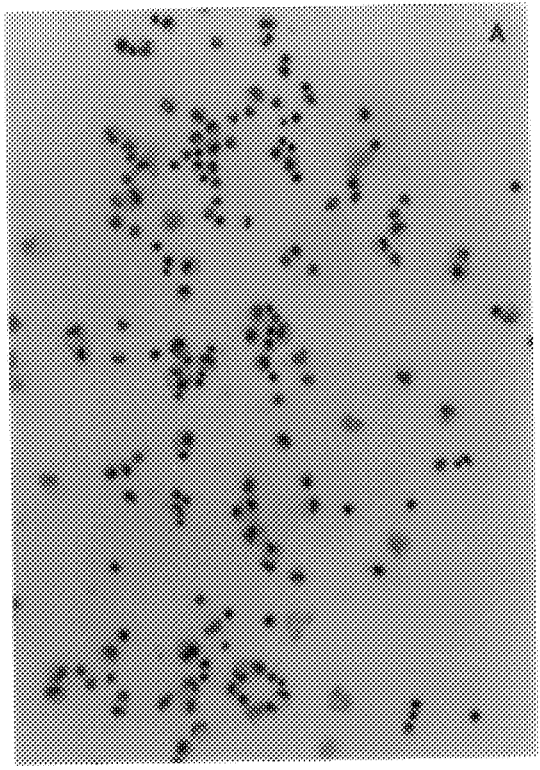
FIG. 14A
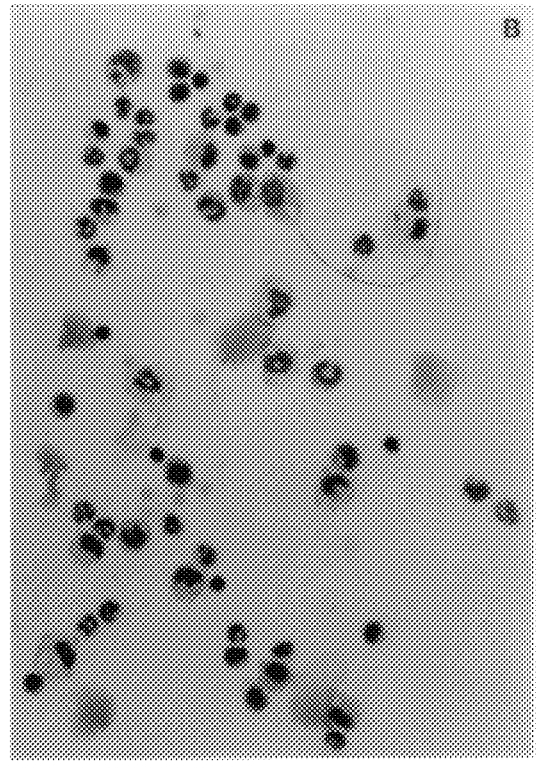
FIG. 14B
FIG. 14C
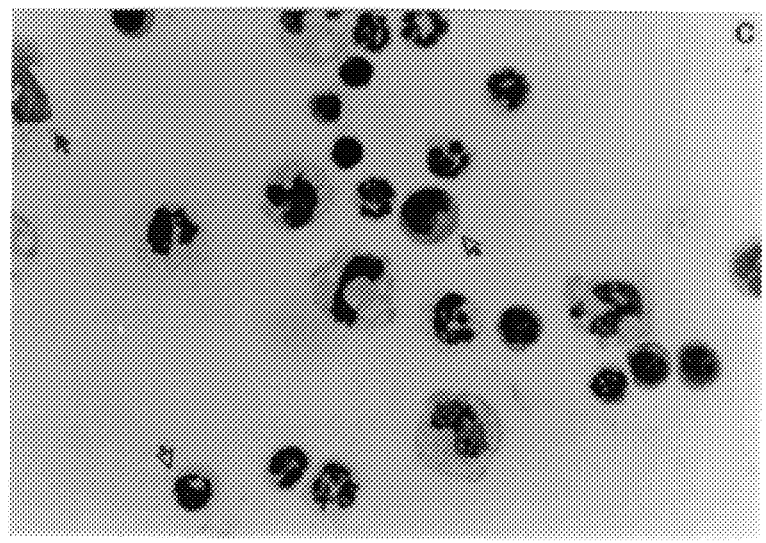

ANTI-CANCER COMPOSITIONS

BACKGROUND OF THE INVENTION

1. Field of the Invention

The file of this patent contains at least one drawing executed in color. Copies of this patent with color drawing will be provided by the Patent and Trademark Office upon request and payment of the necessary fee.

The present invention relates to an anti-cancer composition containing acridine derivatives and guanosine compounds. In the composition of the present invention, the acridine derivative and the guanosine compound are present in the weight ratio of 1:0.1–5.0, preferably 1:0.3–3.0 and more preferably 1:0.5–1.5.

2. Background Art

A tumor is a disease in which cells are excessively proliferating for some reasons in the living body. Cancer is a malignant tumor which is thought as being the "progressive, uncontrolled and unlimited proliferation of cells". The uncontrolled proliferation means that cells can continuously proliferate by avoiding physiological surveillance and various suppressive factors in the living body, although some exceptions may be present. Cancerous cells are characterized by low serum requirement and active proliferation even in diluted blood. Cancer cells can produce growth factors which assist unregulated malignant proliferation.

Cancer or neoplasm is a cell population which carries excessive and self-regulating proliferation to invade the living body, and the malignant tumor tends to invade the healthy tissues resulting in infiltrating proliferation. In addition, the cancer cells may be shed and disseminated to other organs and tissues through blood or lymph node, resulting in the formation of the secondary cancer (i.e., metastasized cancer). Metastatic cancer in the human body is one of the most fatal diseases which produces an extremely high mortality and causes intolerable pain. Currently the incidence of cancer keeps increasing.

Advances in molecular and cellular biology of cancer have revealed that oncogenes and tumor suppressor genes are involved in the induction of neoplasms and that carcinogenesis is also associated with the intervention of signal transduction systems, which affect cell proliferation, genes and regulatory systems of gene expression, and the like. When oncogenes are activated, an increase in expression and cell division occurrs, whereas tumor suppressor genes are generally involved in suppression of cell division and proliferation. It is generally accepted that cancer cells with unlimited proliferation are expressed due to a certain abnormality of the proliferation stop mechanism which involves proliferative factors, proliferation inhibiting factors, intracellular substrates, cell surface molecules, and the like.

At present, it is well known that chemotherapeutic agents currently used for the treatment of malignant tumors have limitations in clinical applications due to their serious adverse effects such as bone marrow suppression and gastrointestinal disturbances, and thus cannot sufficiently provide successful treatment of cancer. Furthermore, more potent cancer chemotherapeutic agents exhibit more serious toxicities, unpleasant feelings and intoxications, etc., besides the symptoms resulting from cancer itself. Currently, the treatment of cancer includes surgery, radiotherapy, chemotherapy, endocrinological therapy, immunological therapy, and the like. Anti-cancer agents being used for treatment of a malignant tumor may kill normal cells as well as cancerous cells. Because of this non-specific cytotoxicity, anti-cancer agents not only kill or destroy cancer cells but also destroy rapid proliferative tissues such as bone marrow, lymphatic tissue, epithelial cells of oral cavity and stomach, skin, epithelium of genital glands, etc. Furthermore, when anti-cancer agents are repetitively administered, they can cause many disorders of the organs and tissues, immunodepression, teratogenicity, carcinogenicity, and the like.

Since cancer cells are difficult to destroy by means of one chemotherapeutic agent due to the heterogeneity of human malignant tumors and drug resistance, it is preferable to inhibit the proliferation of cancer cells at all stages by combined therapy of two or more chemotherapeutic agents, each of which affects a different stage in cell proliferation. Accordingly, many attempts have been made to effectively inhibit tumor proliferation, and at the same time to reduce the harmful side effects by such combined therapy.

In this aspect, the present inventors have performed extensive experimental studies using a number of compounds. Pharmacological and pathological examinations allowed us to reveal that acridine derivatives and guanosine compounds are effective against tumor growth. We found that either acridine derivatives or guanosine compounds have extremely low anti-cancer activity when used alone, whereas the two agents in combination exhibit an excellent anti-cancer effect. Thus, we have completed the present invention relating to the composition containing acridine derivatives and guanosine compounds, which acts against cancer.

Accordingly, it is an object of the present invention to provide an anti-cancer composition containing an acridine derivative and a guanosine compound.

The second object of the present invention is to provide an anti-cancer composition containing acriflavine neutral and guanosine hydrate as active ingredients.

The third object of the present invention is to provide an anti-cancer composition containing an acridine derivative and a guanosine compound in the weight ratio of 1:0.1–5.0, preferably 1:0.3–3.0 and more preferably 1:0.5–1.5.

The foregoing has outlined some of the more pertinent objects of the present invention. These objects should be construed to be merely illustrative of some of the more pertinent features ana applications of the invention. Other many beneficial results can be obtained by applying the disclosed invention in a different manner or modifying the invention within the scope of the disclosure. Accordingly, other objects and a more thorough understanding of the invention may be had by referring to the disclosure of invention and the accompanying drawings, in addition to the scope of the invention by the claims.

BRIEF DESCRIPTION OF THE DRAWINGS

For a thorough understanding of the nature and objects of the invention, reference should be had to the following detailed description taken in connection with the accompanying drawings in which:

FIGS. 8A, 8B, and 8C are photographs showing the disappearance of cancer cells and appearance of normal tissues with the anti-cancer composition(AG60) of the present invention in mouse peritoneum into which Ehrlich ascitic cancer cells are transplanted [⇐: normal cells, A: X10, B: X20, C: X40];

FIGS. 10A, 10B and 10C are photographs showing the colony formation of P388 leukemic cells in mouse peritoneum into which P388 leukemic cells are transplanted, as the control group [← cancer cell colony, A: X10, B: X20, C: X40];

FIGS. 11A, 11B and 11C are photographs showing the disappearance of P388 cells and appearance of normal cells with the anti-cancer composition(AG60) of the present invention in mouse peritoneum into which P388 leukemic cells are transplanted [⇐: normal cells, ◄: disappearance of cancer cells, A: X10, B: X20, C: X40];

FIGS. 13A, 13B and 13C are photographs showing the colony formation of L1210 cells in mouse peritoneum into which L1210 leukemic cells are transplanted, as the control group [←: cancer cell colony, A: X10, B: C20, C: X40];

FIGS. 14A, 14B and 14C are photographs showing the disappearance of L1210 cells and appearance of normal cells with the anti-cancer composition(AG60) of the present invention in mouse peritoneum into which L1210 leukemic cells are transplanted [⇐: normal cells, ◄: disappearance of cancer cells, A: X10, B: X20, C: X40];

DISCLOSURE OF INVENTION

Figure 1A:
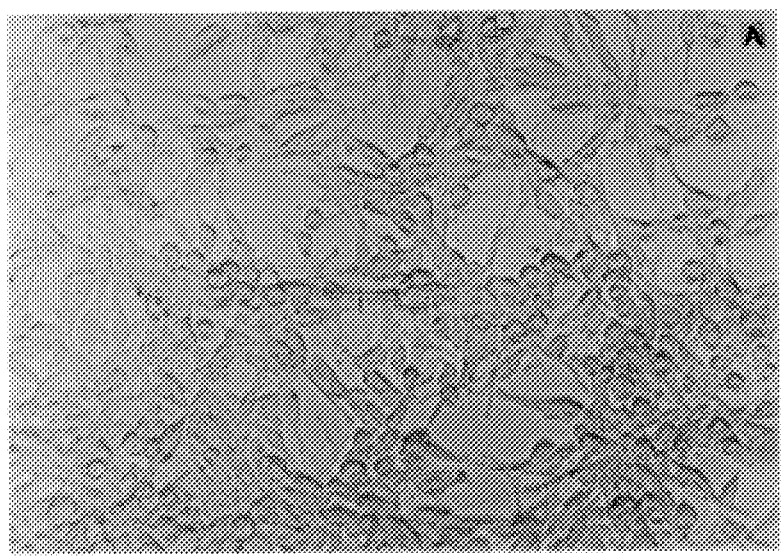
FIGS. 1A, 1B, 1C and 1D are photographs comparing the effect of the anti-cancer composition(AG60) of the present invention, acriflavine neutral and guanosine hydrate, on the cell survival rate of lung cancer cell lines(3LL) [A: control group, B: acriflavine neutral 100 $\mu$g/ml, C: guanosine hydrate 2 mg/ml, D: the present composition(AG60)100 $\mu$g/ml]
Figure 1B:
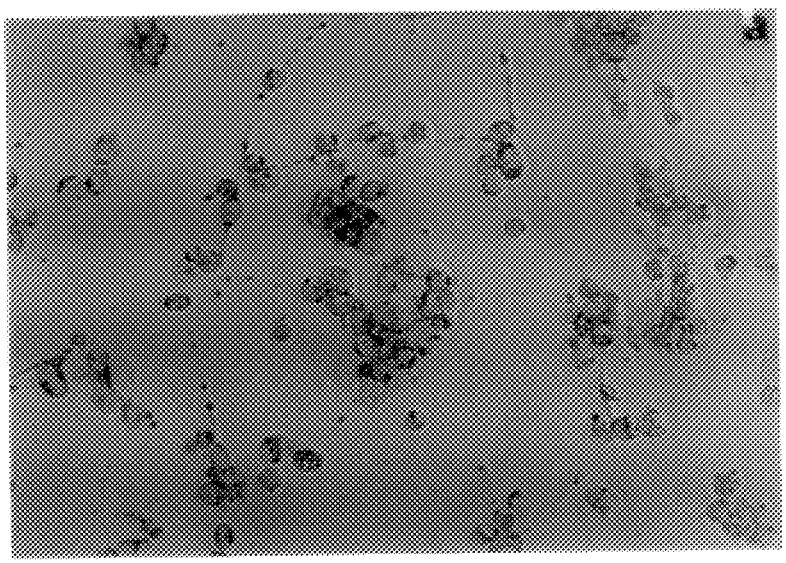
Figure 1C:
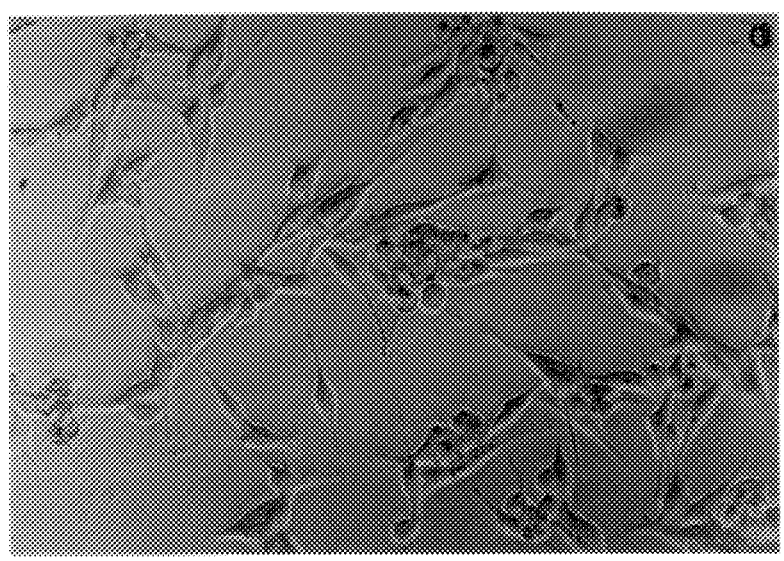
Figure 1D:
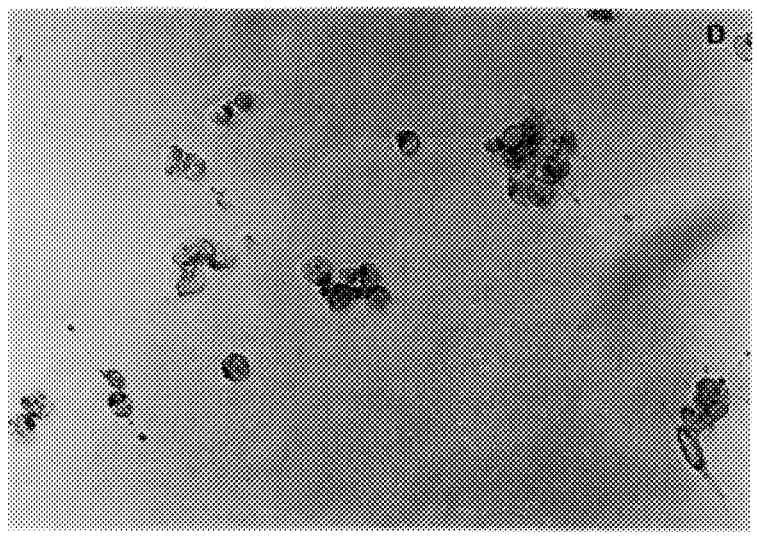
Figure 2A:
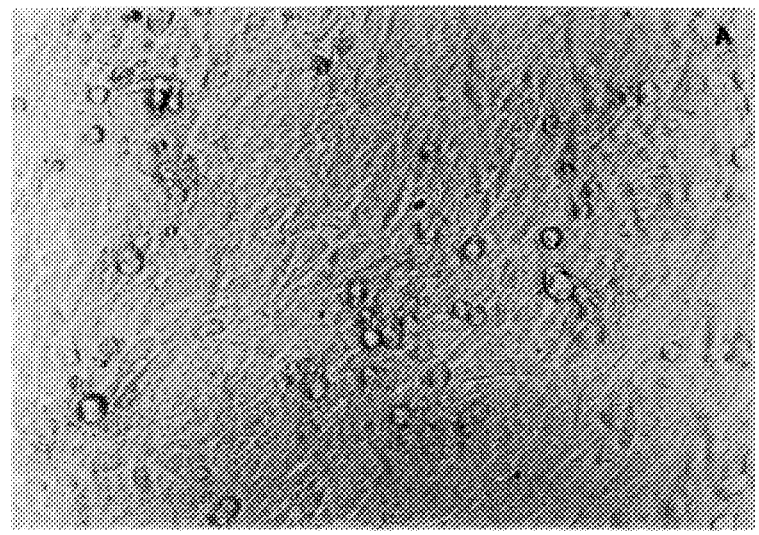
FIGS. 2A, 2B, 2C and 2D are photographs comparing the effect of the anti-cancer composition(AG60) of the present invention, acriflavine neutral and guanosine hydrate, on the cell survival rate of hepatome cell lines((SK-HEP-1) [A: control group, B: acriflavine neutral 100 µg/ml, C: guanosine hydrate 2 mg/ml, D: the present composition(AG60) 100 µg/ml]
Figure 2B:
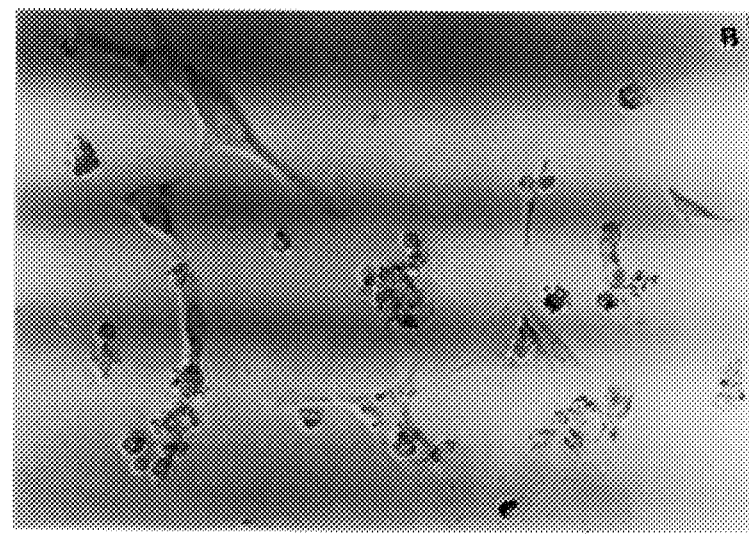
Figure 2C:
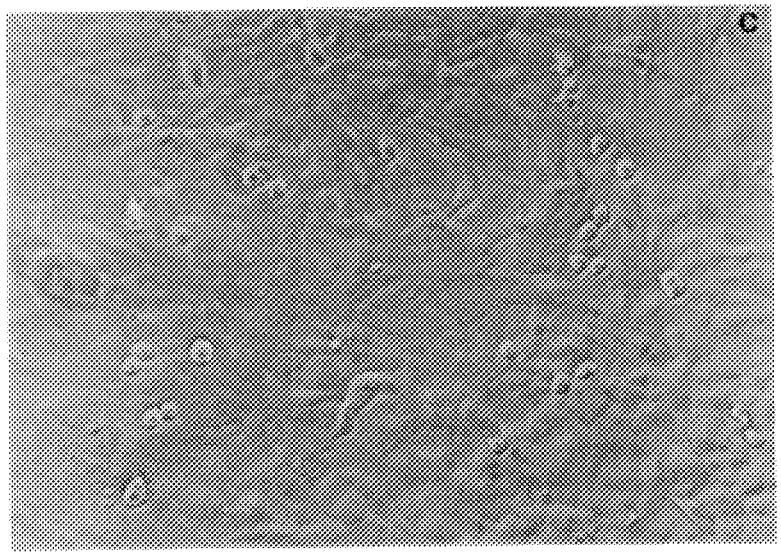
Figure 2D:
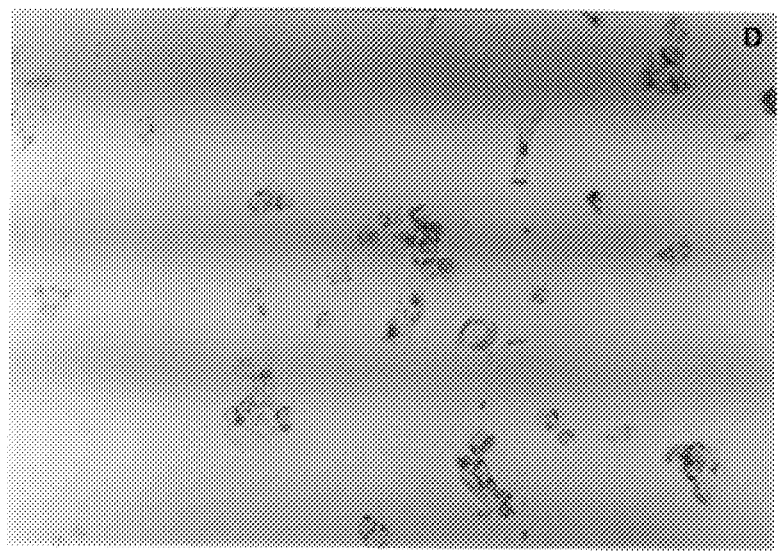
Figure 3A:
FIGS. 3A, 3B, 3C and 3D are photographs showing a pathological view of kideny, lung, liver and spleen tissues of mice to which the anti-cancer composition(AG60) of the present invention is administered [A: kideny tissue, B: lung tissue, C: liver tissue, D: spleen tissue]
Figure 3B:
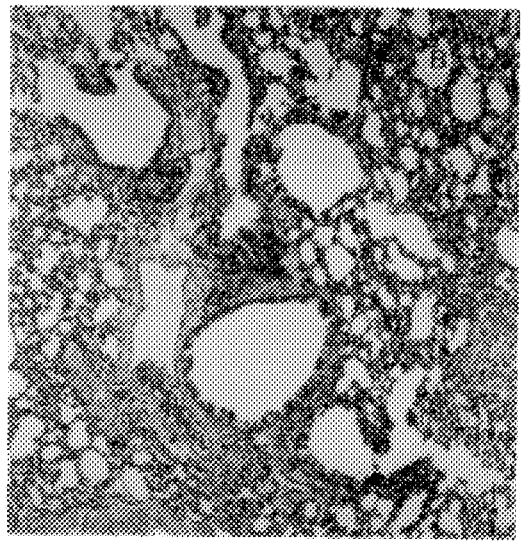
Figure 3C:
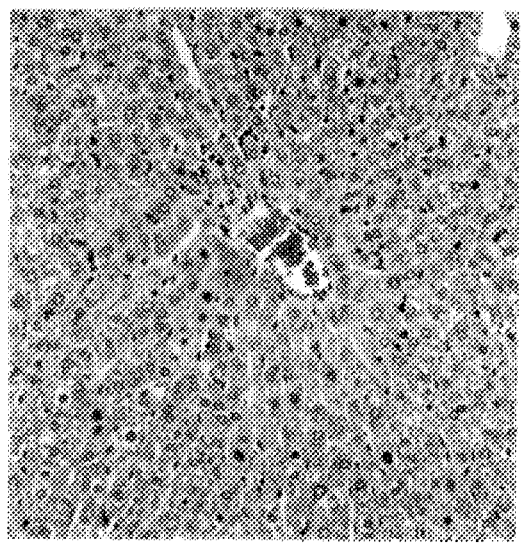
Figure 3D:
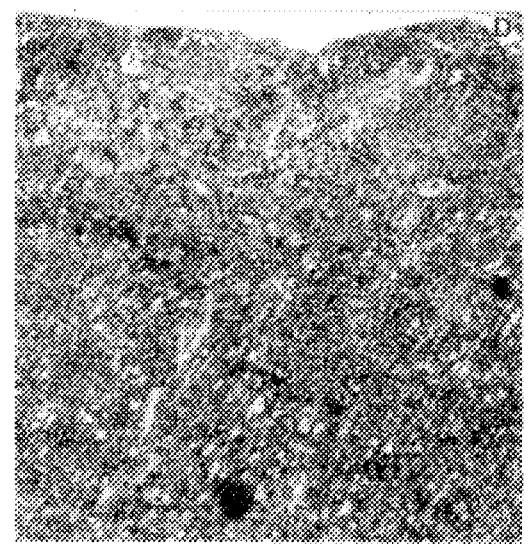

In one aspect, the present invention relates to an anti-cancer composition containing an acridine derivative and a guanosine compound as active ingredients.

The acridine derivative as one effective component of the composition according to the present invention includes acriflavine, acriflavine neutral, acridine orange, acridine yellow G, diacridine, aniline mustard, salts thereof, and the like, with acriflavine neutral being most preferable. Acriflavine neutral as one of the acridine derivatives is a compound composed of 3,6diamino-10-methylacridium chloride and 3,6-diaminoacridine in the mixing ratio of approximately 1:1 and is a yellowish-brown powder having the following chemical structure:

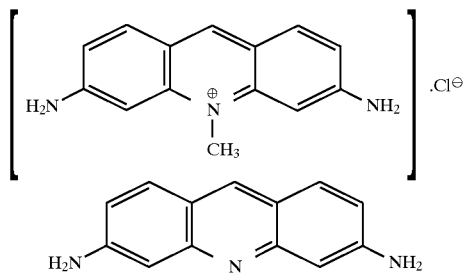

Acriflavine neutral which is most preferably used as the acridine derivative in the present invention is a dye having an acridine nucleus and has a week basic property, and is fluorescent in aqueous solution. This compound has been used as an anti-malarial, anti-tripanosomal or bactericidal agent and inhibits the growth of microorganisms generally at the concentrations of $10^{-4}$ to $10^{-5}$M. Since Ehrlich synthesized acriflavine neutral from acridine nucleus in 1912, anti-tripanosomal activity of the agent has been found. Thus, acriflavine neutral has been used externally or systemically for treatment of purulent diseases due to its potent antibacterial activity. Acriflavine neutral has a low toxicity at the clinically used dosage range, although the agent weakly irritates mucous membranes. Thus, it can be used in the form of injectable or enteral medicines. In contrast to other antibacterial agents, acriflavine neutral is characterized by its antibacterial activity which is not lowered in the presence of serum proteins, blood, etc. Furthermore, acriflavine neutral has a strong entry deep of action and a rapid onset of action, and does not suppress the hematopoietic system, nor damage the liver, etc., following repetitive administrations for a prolonged period.

The mechanism of action of acriflavine neutral against microorganisms is not firmly established. However, it has been reported that since the structure of acriflavine neutral is similar to that of riboflavine (vitamine $B_2$), acriflavine neutral inhibits diamino acid oxidase, etc., as the enzyme present in trypanosoma, due to metabolic antagonistic activity, and is ionized in the living body to produce a cationic part which inhibits bacterial respiratory enzymes [see, Keigiro Takaki, Pharmacology (Japan), p617, 1989].

The guanosine compound as the second effective component of the composition according to the present invention includes guanosine, guanosine hydrate, isoguanosine, and salts and mixture thereof, etc., with guanosine hydrate being the most preferable. Guanosine is the compound represented as follows: chemical name 2-amino-9-β-D-ribofuranosyl-9H-purin-6-(1H)-one, molecular formula $C_{10}H_{13}N_5O_5$, molecular weight 283.24. Guanosine, which is formed by combining guanine and D-ribose with β-linkage, is part of guanosine nucleotides. Guanosine can be synthesized either by polymerization of a guanine derivative with a D-ribose derivative or by dephosphorylation of guanilic acid. Guanosine is decomposed at its melting point of 240° C. and has a specific optical density of $[\alpha]_D^{20}=60.5°(3\%, 0.1N\ NaOH)$, and UV spectrum of $\lambda_{max}$ 256 nm($\epsilon$ max $13.6\times10^3$) and $\lambda_{min}$ 228 nm at pH 7 and $\lambda_{max}$ 253 nm ($\epsilon$ max $13.6\times10^3$) and $\lambda_{min}$ 223 nm at pH 6 [AS 118-0-0-3]. Guanosine hydrate is the hydrated form of guanosine and has the following chemical structure:

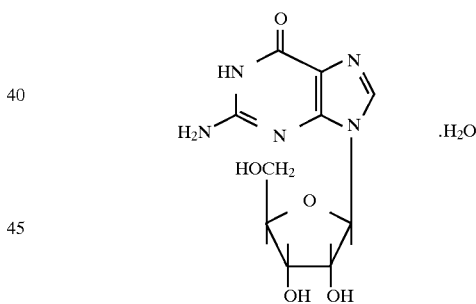

In guanosine hydrate, 9-position of guanine is bonded to 1-position of D-ribose with N-glucoside linkage. Guanosine exhibits the maximum absorption at 256 nm and is slighly soluble in cold water but soluble in warm water. Guanosine is converted into xanthine by deamination and is decomposed into ribose-1-phosphoric acid and hypoxanthine by nucleoside phosphorylase. In living body, guanosine is produced from guanilic acid by the action of 5'-nucleoside and is hydrolysed to guanine by the action of nucleoside phosphorylase.

The active form of NAD(nicotineamide adenine dinucleotide), which is the cellular cofactor acting on guanosine metabolism, is the co-enzyme for many dehydrogenases including alcohol dehydrogenase and is converted into the reduced form of hydrogen ion in the substrate, which is then directly introduced into the pyridine nucleus to form NADH(reductive form of NAD) or DPNH(reductive form of DPN). The binding of NAD with apo enzyme requires $Zn^+$.

When dueterium is introduced into this reaction, the reaction is conducted as follows: $CH_7CO_2O_2OH+NAD^+ \leftrightarrows CH_2CDD+NADD+H^+$. In this reaction, deuterium is introduced into the 4 position. When pyridine is removed by the action of enzyme, the stereospecificity of NAD is changed and then niacin, which is an antipellagra factor, is biosynthesized from $NAD^+$ in the animal body.

According to the present invention, it has been identified that although the acridine derivative and the guanosine compound have low anti-cancer effect when they are used separately, the combination of the two compounds exhibits an excellent anti-cancer effect and has substantially no adverse effects. The present invention has been established on the basis of this finding.

Accordingly, the first object of the present invention is to provide an anti-cancer composition containing an acridine derivative and a guanosine compound as active ingredients. More specifically, the present invention provides a novel pharmaceutical composition for treatment of cancer characterized by an excellent anti-cancer effect obtained from the combination of acriflavine neutral and a guanosine hydrate.

As mentioned above, another object of the present invention is to provide a use of the combination of an acridine derivative and a guanosine compound as an anti-cancer agent.

The combination of acriflavine neutral and guanosine hydrate is characterized by low drug resistance and substantially no side effects.

As described above, many scientists have attempted to conduct numerous in vitro experiments on anti-cancer and antiviral activities of acridine derivatives as used in the composition of the present invention. However, no one has obtained fruitful results as yet. In addition, it has not been reported that guanosine compounds have anti-cancer effect.

In the composition of the present invention, the constitutional ratio of the acridine derivative, particularly acriflavine neutral, and the guanosine compound, particularly guanosine hydrate is 1:0.1–5.0, preferably 1:0.3–3.0 and more preferably 1:0.5–1.5.

The combined composition of the acridine derivative such as acriflavine neutral and the guanosine compound such as guanosine hydrate according to the present invention can be formulated by means of conventional methods for preparing pharmaceutical preparations. For example, acriflavine neutral and guanosine hydrate are mixed in a suitable ratio in a light resistant container and then an effective therapeutic amount of this mixture is alone, or in combination with pharmaceutically acceptable carriers, formulated into the pharmaceutical formulation suitable for parenteral or oral administration which can be parenterally or orally administered to inhibit the growth of a tumor in a human body.

The specific cancers which can be treated with the composition of the present invention can include lung cancer, hepatoma, leukemia, solid tumor and carcinomas originated from epithelial tissue.

Although the effective amount of the composition according to the present invention can be varied depending upon various factors including the subject to be administered, severity of cancer to be treated, etc., generally in an adult man (based on a body weight of 60 kg), the dosage may be in the range of 0.5 to 3 mg/kg of body weight, preferably 0.5 to 1.5 mg/kg of body weight, per day for oral administration and in the range of 0.02 to 0.3 mg/kg of body weight, preferably 0.05 to 0.2 mg/kg of body weight, per day for intramuscular injections. Alternatively, the present composition can be administered by intravenous and subcutaneous injections and intravenous infusion.

If necessary, the composition of the present invention can include other medicinal components having immunoadjuvant activity or anti-cancer activity, or can be administered in combination with an other immunoadjuvant or anti-cancer agent.

As the immunoadjuvant which can be included in, or combined with, the composition according to the present invention, the followings can be mentioned: monoclonal antibodies, immunoagitators, human immunoglobulins or interferones, for example, lectins, interferones, interleukins, etc. As the anti-cancer agent which can be used for this purpose, the followings can be mentioned: synthetic anti-cancer agents, for example, alkylating agents such as chlorambucil, melphalan, cyclophosphamide, nitrosourea amine compounds such as mannomustine, ethylenediamines such as uredepa; anti-metabolic agents, for example, folic acid antagonists such as methotrexate, aminoptherine, etc., purine antagonists such as mercaptopurine, pyrimidine antagonists such as proxuridine, 6-azauridine, etc., sugar-based antagonists such as mitobronitol, or cisplatin, picivanil, 5-fluorouracil(5-FU), etc.; anti-cancer antibiotics, for example, actinomycin, THP-adriamycin, mitomycin, etc.; hormone antagonists such as tamoxifen, etc.; and alkaloid plant components such as demecolcine, etc.

Hereinafter, the present invention will be more specifically explained by the following compositions examples and experiments. However, it should be understood that they are provided only for one explanation of the present invention and are not intended to limit the technical scope of the present invention in any manner.

COMPOSITION EXAMPLE 1

| Acriflavine neutral | 60 mg |
|---|---|
| Guanosine hydrate | 60 mg |

In a light resistant container, 60 mg of acriflavine neutral and 60 mg of guanosine hydrate (hereinafter, this mixture is referred to as "AG60") were dissolved in 40 ml of warm distilled water, cooled, adjusted to pH 6.5–7.0 and then sterilized. The resulting sterilized solution is used as an injectable preparation. The injectable preparation of the present invention is warmed approximately to body temperature before use.

COMPOSITION EXAMPLE 2

| Acriflavine neutral | 60 mg |
|---|---|
| Guanosine hydrate | 18 mg |

The said two components were mixed in the same manner as Composition Example 1 to prepare the injectable composition.

COMPOSITION EXAMPLE 3

| Ariflavine neutral | 60 mg |
|---|---|
| Guanosine hydrate | 60 mg |

The said two components were mixed in the same manner as Composition Example 1 to prepare the injectable composition.

COMPOSITION EXAMPLE 4

| Acriflavine neutral | 60 mg |
|---|---|
| Guanosine hydrate | 120 mg |

The said two components were mixed in the same manner as Composition Example 1 to prepare the injectable composition.

COMPOSITION EXAMPLE 5

| Acriflavine neutral | 60 mg |
|---|---|
| Guanosine hydrate | 240 mg |

The said two components were mixed in the same manner as Composition Example 1 to prepare the injectable composition.

COMPOSITION EXAMPLE 6

| Acriflavine neutral | 600 mg |
|---|---|
| Guanosine hydrate | 600 mg |

The said two components were mixed in a light resistant container and the resulting composition was used to fill several capsules to prepare the capsule preparation for oral use.

Experiment 1
In vitro test for the effect of the composition (AG60) of the present invention on mouse lung cancer cells 3LL and human hepatoma cells SK-HEP-1

Cancer cells used for this test include human hepatoma cell line SK-HEP-1 and mouse lung cancer cell line 3LL, as recommended by the U.S. NCI(National Cancer Institute).

These cell lines were incubated in the culture media prepared by adding 10% inactivated FBS(fetal bovine serum), 100 μg/ml of streptomycin and 100 units/ml of penicillin to RPMI 1640 medium, at 37° C. in an incubator (Heraus) under 5% $CO_2$ and 100% humidity. According to the result of examination on the linear growth of each cell, 3LL and SK-HEP-1 cells were inoculated in an amount of $2.5 \times 10^3$ cells and $1 \times 10^4$ cells, respectively, into each well of 96 well plate and then incubated for 24 hours. Each of the composition (AG60) of the present invention and acriflavine neutral in an amount of 100, 10, 1, 0.5, 0.25, 0.125, 0.0625 μg/ml and guanosine hydrate in an amount of 2000, 1000, 100, 5, 2.5, 1.25 μg/ml were added thereto. After 2 days, the survival rate of cells was calculated by carrying out MTT method using determination of dehydrogenase enzyme in cellular mitochondria and measuring the absorbance at 540 nm by means of a spectrophotometer (ELISA reader), to determine the anti-cancer activity of the composition according to the present invention against respective cancer cells. MTT test is a method in which formazan precipitate formed by reduction of MTT with cellular mitochondria dehydrogenase in living cells is dissolved and then the absorbance is measured. Thus, since in vigorously dividing cancer cells the enzyme is fully active, by the action of enzyme MTT is reduced to form the precipitate which can be dissolved to determine the absorbance, thereby identifying the survival rate of respective cells. The survival rate of cells was calculated according to the following equation:

$$\text{Survival rate} = \frac{\text{Absorbance in the test group}}{\text{Absorbance in the control group}} \times 100$$

As the survival rate, ID values against lung cancer cell lines 3LL and hepatoma cell lines SK-HEP-1 were determined as 15.776 μg/ml and 18.025 μg/ml, respectively, for the composition (AG60) of the present invention; 20.1162 g/ml and 27.12 μg/ml, respectively, for acriflavine neutral; and 1518.1940 μg/ml and 1530.78 μg/ml, respectively, for guanosine hydrate.

Although the cytotoxicities of the composition(AG60) of the present invention against cell lines used in this experiment are somewhat different from each other, as shown in FIG. 1 (photograph for lung cancer cell lines 3LL) and FIG. 2 (photograph for hepatoma cell lines (SK-HEP-1), the composition (AG60) of the present invention, which is the combination of acriflavine neutral and guanosine hydrate, shows an increased cytotoxicity to inhibit the cell proliferation and destroy the cells, in comparison with each of acriflavine neutral and guanosine hydrate. When either acriflavine neutral or guanosine hydrate was used alone, only acriflavine neutral showed anti-cancer activity but guanosine hydrate did not show any anti-cancer activity. From this result, it can be supposed that guanosine hydrate increases the anti-cancer activity of acriflavine neutral.

Experiment 2
Toxicity test for the composition(AG60) of the present invention in mouse 1) Determination of $LD_{50}$(50% lethal dose) of the composition (AG60) of the present invention in mouse:

Normal 30 ICR mice(♀, 20±1 g) were divided into 5 groups such that each group included 6 mice. The composition(AG60) of the present invention was intraperitoneally administered in an amount of 30 mg/kg to the group A, 50 mg/kg to the group B, 75 mg/kg to the group C, 80 mg/kg to the group D and 100 mg/kg to the group E and then the death rate of animals was observed within 5 days after the administration.

The results as observed are shown in the following Table 1. As can be seen from Table 1, none of mice in the group A(30 mg/kg) died, but one mouse in the group B(75 mg/kg), 3 mice in the group C(75 mg/kg), 4 mice in the group D(80 mg/kg) and all of 6 mice in the group E(100 mg/kg) died. According to this result, it can be determined that the $LD_{50}$ value of the composition(AG60) of the present invention is 68.08 mg/kg/i.p.

TABLE 1

| | $LD_{50}$ value of the composition(AG60) of the present invention in mouse | | | |
|---|---|---|---|---|
| Group | Dose(mg/kg) | Dead animals/Tested animals | *Z | **d |
| A | 30 | 0/6 | | |
| | | > | 0.5 | 20 |
| B | 50 | 1/6 | | |
| | | > | 2.0 | 15 |
| C | 65 | 3/6 | | |
| | | > | 3.5 | 15 |
| D | 80 | 4/6 | | |
| | | > | 5.0 | 20 |
| E | 100 | 6/6 | | |

Note)
*Z: half(½) of the number of animals died at the successive two doses
**d: difference between the successive two doses LD$_{50}$ of the composition(AG60) of the present invention:

$$LD_{50} = LD_{100} - \frac{\Sigma Zd}{\text{Number of tested animals}} = 68.08 \text{ mg/kg/i.p.}$$

2) Histopathological examination for intraperitoneal administration of the composition(AG60) of the present invention:

Normal 10 ICR mice(♀, 20±1 g) were divided into two groups such that each group included 5 mice. The group A received physiological saline in an amount of 10 ml/kg and the group B received the composition(AG60) of the present invention in an amount of 30 mg/kg, in which the physiological saline and the present composition were intraperitoneally administered once a day over three times. After 2 days from the termination of administration, mice were killed and then liver, kidney, lung and spleen were removed. The excised organs were fixed in 10% formalin to prepare the pathological tissue samples which were then used to conduct the histopathological examinations. According to this, it could be found that the kidney glomeruli and tubules were well retained and had no pathological changes, and in the lung tissue alveoli and bronchiolar epithelial cells were well retained and were also pathologically normal. In addition, in the liver tissue central veins, hepatocytes and Kupffer cells were normal in a pathological view, and the spleen tissue was also normal.

3) Histopathological examination for intramuscular administration of the composition(AG60) of the present invention:

Normal 10 ICR mice(♀, 20±1 g) were divided into two groups such that each group included 5 mice. The group A received physiological saline in an amount of 10 ml/kg and the group B received the composition(AG60) of the present invention in an amount of 30 mg/kg, in which the physiological saline and the present composition were intramuscularly administered once a day over three times. After 2 days from the termination of administration, the mice were killed and then liver, kidney, lung and spleen were removed from the mice. The separated organs were fixed in 10% formalin and then subjected to H&E staining (hematoxylin and eosin staining) to prepare the pathological tissue samples which were then used to conduct the histopathological examinations. The results thereof are shown in FIG. 3. According to the results, it could be found that the glomeruli and tubules of the kidney tissue were well retained and had no pathological change, and in the lung tissue alveoli and bronchiolar epithelial cells were well retained and were also normal in a pathological view. In addition, in the liver tissue central vein, liver cells and Kupffer cells were normal in a pathological view, and the spleen tissue was also normal.

4) Hematological examination:

This test was conducted according to the same manner as the above test 2). After 2 days from the termination of administration of the composition(AG60) of the present invention, blood was collected to conduct the histological examination in which the changes in hemoglobin(Hb), hematocrit(HT), erythrocyte(RBC) and leukocyte(WBC) were measured.

The result as measured is shown in the following Table 2. As can be seen from Table 2, in comparison with the control group the group to which the composition(AG60) of the present invention was administered showed an increase in the level of hemoglobin, hematocrit and erythrocyte and retained the level of leukocyte within the normal range.

TABLE 2

Hematological examination in mouse to which the composition(AG60) of the present invention is administered

| Test Group | Hb(g/dl) | HT(%) | RBC(× 10$^6$) | WBC(× 10$^6$) |
|---|---|---|---|---|
| A | 6.7 | 19.0 | 226.5 | 6875 |
| B | 9.4 | 28.0 | 313.5 | 5995 |

Note)
A: control group
B: the group to which the composition(AG60) of the present invention is adminsitered Experiment 3

Comparative test for inhibition of Ehrlich solid tumor proliferation with acriflavine neutral(An), guanosine hydrate (Gh) and the composition(AG60) of the present invention Normal 20 ICR mice(♂, 20±1 g) were divided into 4 groups such that each group included 5 mice. Ehrlich cancer cells were transplanted into the inguinal area of all experimental animals in an amount of 1×10$^7$ cells per animal. After 24 hours, the control group A received physiological saline in an amount of 10 ml/kg by intramuscular injection, once a day, for 15 days. As the comparative groups, the groups B and C received acriflavine neutral(An) in an amount of 15 mg/kg and guanosine hydrate(Gh) in an amount of 15 mg/kg, respectively, in the same manner as the control group. To the group D the composition (AG60) of the present invention was administered in an amount of 30 mg/kg in the same manner as the control group. During 15 days after the transplantation of cancer cells the proliferation of solid tumor in each group was observed.

Figure 4:
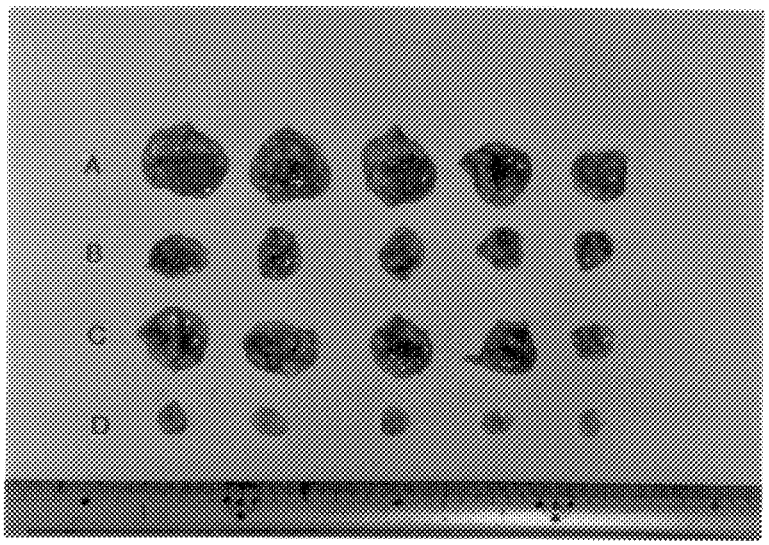
FIG. 4 is a photograph comparing the effect of the anti-cancer composition(AG60) of the present invention, acriflavine neutral and guanosine hydrate, on cancer cell proliferation in mice into which Ehrlich cancer cells are transplanted [A: control group, physiological saline 10 ml/kg/i.m., B: acriflavine neutral 15 mg/kg/i.m., C: guanosine hydrate 15 mg/kg/ i.m., D: the present composition (AG60) 30 mg/kg/i.m.]
Figure 6A:
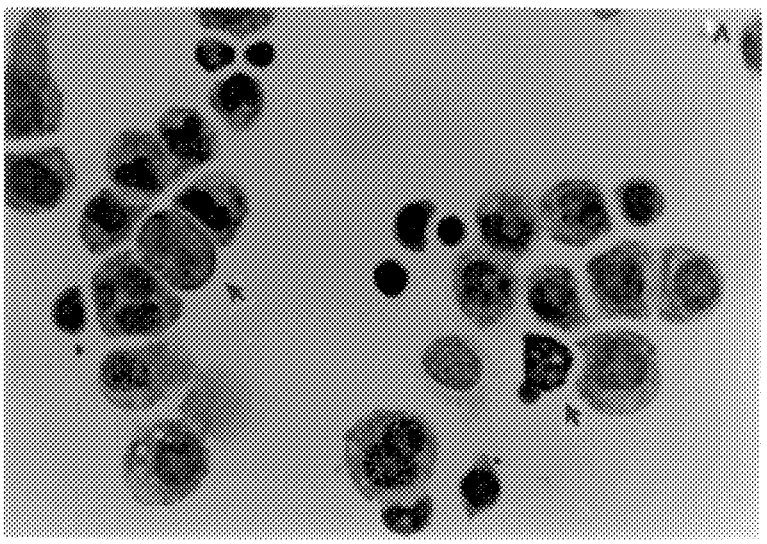
FIGS. 6A, 6B, 6C, 6D and 6E are photographs showing the determination of the effective dose of the anti-cancer composition(AG60) of the present invention which exhibits inhibition or elimination of proliferation of P388 leukemic cells [←: P388 cancer cells, ⇐: normal cells, ◄: necrotized cancer cells, A: control group, physiological saline 10 ml/kg/i.m., B: the present composition (AG60) 10 mg/kg/i.m., C: the present composition(AG60) 20 mg/kg/ i.m., D: the present composition(AG60) 30 mg/kg/i.m., E: the present composition(AG60) 40 mg/kg/i.m.]
Figure 6B:
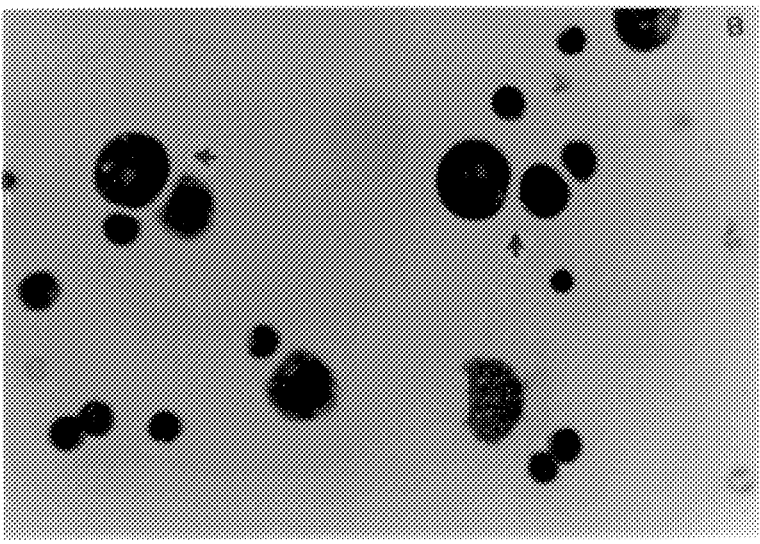
Figure 5:
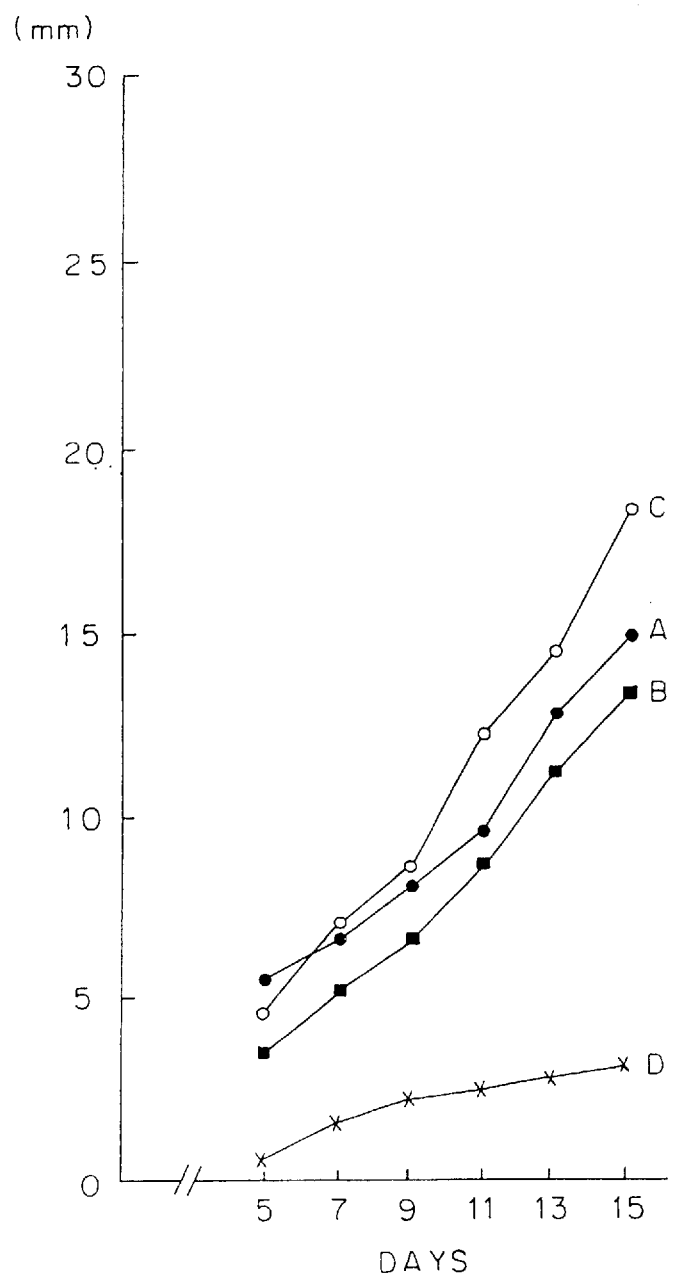
FIG. 5 is a photograph comparing the effect of the anti-cancer composition(AG60) of the present invention, acriflavine neutral and guanosine hydrate, on the size of cancer cells in mice into which Ehrlich cancer cells are transplanted [A: control group, physiological saline 10 ml/kg/i.m., B: acriflavine neutral 15 mg/kg/i.m., C: guanosine hydrate 15 mg/kg/ i.m., D: the present composition (AG60) 30 mg/kg/i.m.]
Figure 6C:
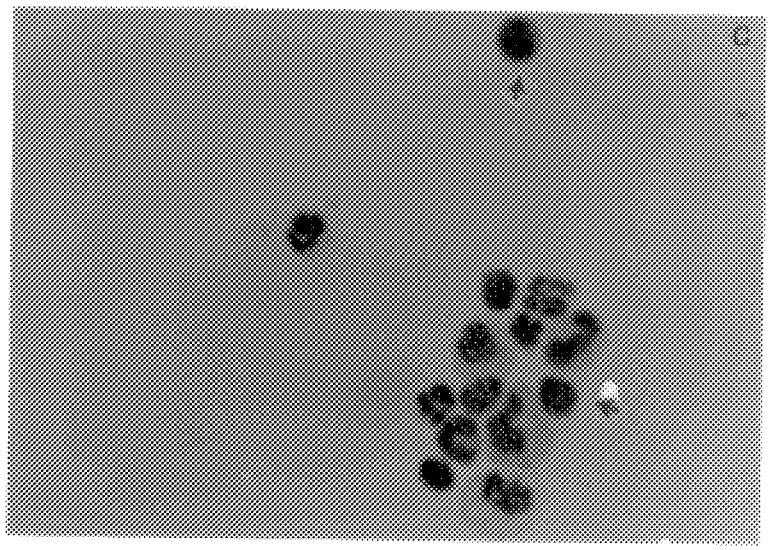
Figure 6D:
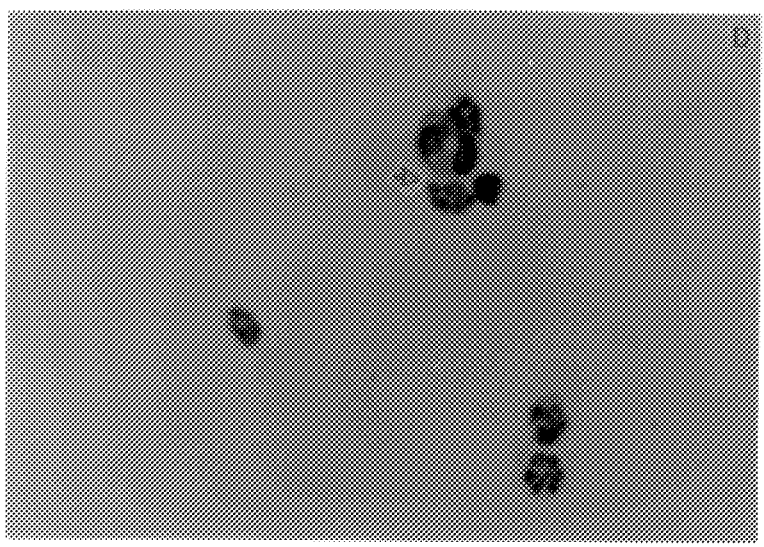
Figure 6E:
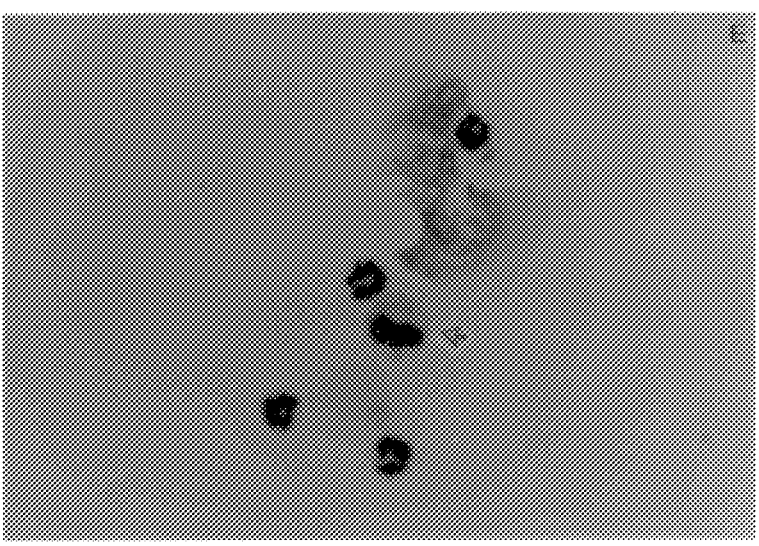

The results thereof are shown in Table 3 and FIGS. 4 and 5. As can be seen from FIG. 4, the proliferation of cancer cells in the acriflavine neutral(An) group B was slightly inhibited as compared with that in the control group, but the guanosine hydrate(Gh) group C and the control group A showed the similar proliferation pattern to each other. However, it could be identified that in group D, to which composition(AG60) of the present invention was administered, the proliferation of the solid tumor was significantly inhibited. That is, the single administration of either acriflavine neutral(An) or guanosine hydrate (Gh) did not provide a remarkable anti-cancer effect and the administration of the combination of the above two compounds, i.e. the composition(AG60) of the present invention provided an excellent anti-cancer effect.

The effects on the solid tumor proliferation of the composition(AG60) of the present invention, acriflavine neutral(An) and guanosine hydrate(Gh) were determined by measuring the size of cancer tissues in control group A, the acriflavine neutral group B, the guanosine hydrate group C and the present composition(AG60) group D from the fifth day to the fifteenth day after the transplantation of cancer cells at an interval of 2 days, and are presented in Table 3 and FIG. 5. As can be seen from Table 3 and FIG. 5, the size of tumor volume in the control group A was 5.6 mm, which is equivalent to an average 2.2 mm increase per every 2 days. The acriflavine neutral group B showed a minor inhibition of cancer proliferation which is greater than the inhibition in the guanosine hydrate-treated group C. In group D to which the composition(AG60) of the present invention was administered, the size of cancer tissue was measured as 1.5 mm after 5 days from transplantation and, thereafter, increased 0.35 mm every 2 days. Accordingly, it could be identified that the inhibition of cancer proliferation in group D treated with the present composition was significantly higher than that in control group A, the acriflavine-treated group B and the guanosine hydrate-treated group C.

TABLE 3

Effect of the composition(AG60) of the present invention and An and Gh on the solid tumor proliferation

| Groups | Days | | | | | |
|---|---|---|---|---|---|---|
| | 5 | 7 | 9 | 11 | 13 | 15 |
| A(control group) | 5.6 | 6.7 | 6.1 | 9.8 | 13.0 | 15.0 |
| B(An) (15 mg/kg) | 3.8 | 5.1 | 6.7 | 8.9 | 11.2 | 13.5 |
| C(Gh) (15 mg/kg) | 4.7 | 6.8 | 8.5 | 12.3 | 14.5 | 18.2 |
| D(AG60) (30 mg/kg) | 1.5 | 1.9 | 2.2 | 2.5 | 2.8 | 3.1 |

Experiment 4

Determination of the optimal effective dose of the composition(AG60) of the present invention for inhibition of P388 leukemic cell proliferation or disappearance of cancer cells Normal 15 $CDF_1$ mice(♀, 20±1 g) were divided into 5 groups such that each group included 3 mice. P388 leukemic cells were transplanted into the peritoneum of each experimental animal in an amount of 1×10⁶ cells per animal. At 24 hours after transplantation, control group A received physiological saline in an amount of 10 ml/kg by intraperitoneal injection once a day, for 3 days. The remaining groups B, C, D and E received the composition(AG60) of the present invention in an amount of 10 mg/kg, 20 mg/kg, 30 mg/kg and 40 mg/kg, respectively, in the same manner as control group A. At 2 days after termination of administration, all experimental animals of each group were killed and peritoneal ascitic fluid was removed, plated and then subjected to Giemsa staining to prepare the smear samples, which were used to determine the effects of the composition(AG60) of the present invention on inhibition of P388 leukemic cell proliferation or disappearance of cancer cells from the dose of 10 mg/kg through 40 mg/kg.

The results as determined are presented in the following Table 4 and FIG. 6. As can be seen from Table 4 and FIG. 6, group B to which the composition(AG60) of the present invention was administered at the dose of 10 mg/kg showed a slight proliferation (+) of P388 leukemic cells and group C to which the composition(AG60) of the present invention was administered in an amount of 20 mg/kg showed inhibition (++) of P388 leukemic cell proliferation due to the anti-cancer effect of the present composition(AG60). In group D or E to which the composition(AG60) of the present invention was administered at the dose of 30 mg/kg or 40 mg/kg, respectively, P388 leukemic cells were not found in mouse peritoneum due to the administration of optimal dose of the present composition(AG60) (+++). Accordingly, the optimal effective dose of the composition(AG60) of the present invention was determined to be 30 mg/kg.

TABLE 4

Optimal effective dose of the composition(AG60) of the present invention for inhibition of P388 leukemic cell proliferation

| Test Group | Dose (mg/kg) | Anti-cancer effect | Observation of cancer cells |
|---|---|---|---|
| A(control) | 10 ml/kg | – | continued proliferation |
| B | 10 | + | moderate proliferation |
| C | 20 | ++ | slight proliferation |

TABLE 4-continued

Optimal effective dose of the composition(AG60) of the present invention for inhibition of P388 leukemic cell proliferation

| Test Group | Dose (mg/kg) | Anti-cancer effect | Observation of cancer cells |
|---|---|---|---|
| D | 30 | +++ | not observed |
| E | 40 | +++ | not observed |

Experiment 5

Anti-cancer effect of the composition(AG60) of the present invention on Ehrlich ascitic cancer 1) Effect of the composition(AG60) of the present invention on Ehrlich cancer cells:

Normal 14 ICR mice(♀, 20±1 g) were divided into two groups such that each group included 7 mice. Ehrlich cancer cells were transplanted into mouse peritoneum in an amount of 1×10⁷ cells per mouse. After 24 hours from transplantation, control group A received physiological saline in an amount of 10 ml/kg by intraperitoneal injection once a day, for 7 days, and group B received the composition (AG60) of the present invention in an amount of 30 mg/kg in the same manner as control group A. At 2 days after interruption of administration, two mice in each group were killed and then subjected to laparotomy. The serosa was plated and then subjected to Giemsa staining to prepare the smear sample which was then used to examine the proliferation of ascitic cancer.

Figure 7A:
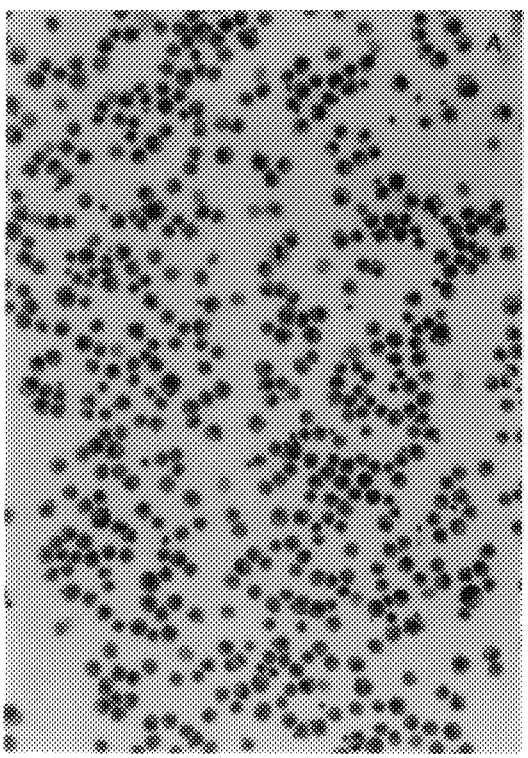
FIGS. 7A, 7B, and 7C are photographs showing colony formation resulting from proliferation of cancer cells in mouse peritoneum into which Ehrlich ascitic cancer cells are transplanted, as the control group [←: cancer cell colony, A: X10, B: X20, C: X40]
Figure 7B:
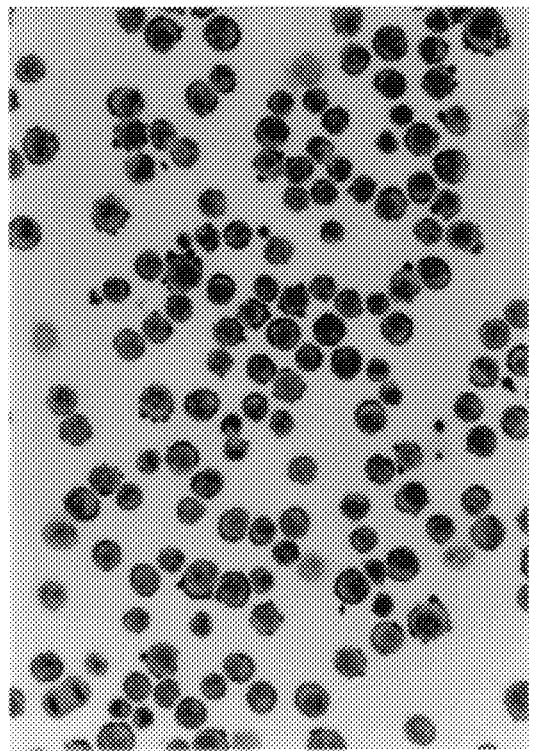
Figure 7C:
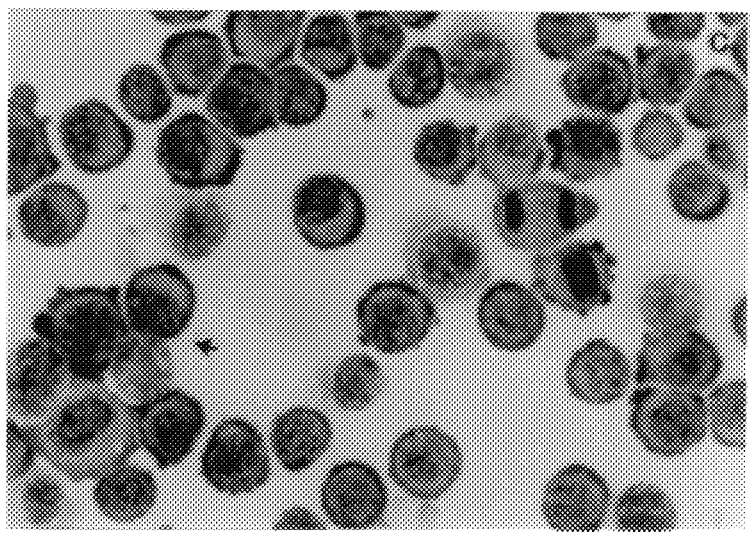

The result thereof is presented in FIGS. 7 and 8. As can be seen from FIGS. 7 and 8, the control group (FIG. 7) showed a continuous proliferation of Ehrlich cancer, but group B (FIG. 8), to which the composition(AG60) of the present invention was administered, showed only normal cells rather than cancer cells.

2) Lifetime extension effects of the composition(AG60) of the present invention in Ehrlich cell-transplanted mice:

To determine the lifetime extension effect of the composition(AG60) of the present invention, 5 mice in each group as survived after the above test 1) were subjected to the same experimental procedure as the above test 1) for 3 days and then the result obtained from group B, to which the present composition(AG60) was administered, was compared with that of the control group A.

Figure 9:
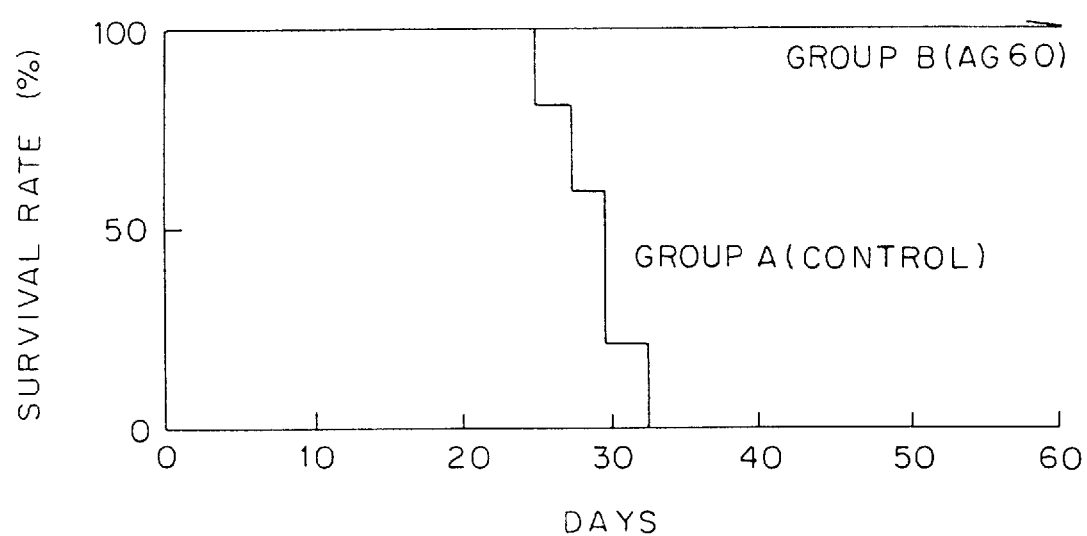
FIG. 9 is a graph showing the lifetime extension effect of the anti-cancer composition(AG60) of the present invention in cancer-transplanted mice [A: control group, physiological saline 10 ml/kg/i.p., B: the present composition(AG60) 30 mg/kg/i.m.]

The result as observed is represented in FIG. 9. As can be seen from FIG. 9, all mice of control group A died due to cancer but all mice of group B, to which the present composition(AG60) was administered, survived over the observed period (60 days).

Experiment 6

Anti-cancer effect of the composition(AG60) of the present invention on P388 leukemia 1) Effect of the composition(AG60) of the present invention on P388 leukemic cells:

Normal 14 $CDF_1$ mice(♂, 20±1 g) were divided into two groups such that each group included 7 mice. P388 leukemic cells were transplanted into mouse peritoneum in an amount of 1×10⁶ cells per mouse. At 24 hours after transplantation, control group A received physiological saline in an amount of 10 ml/kg by intraperitoneal injection once a day, for 7 days, and group B received the composition(AG60) of the present invention in an amount of 30 mg/kg in the same manner as control group A. At 2 days after the interruption of administration, two mice in each group were killed and then subjected to laparotomy. The peritoneal ascitic fluid was plated and then subjected to Giemsa staining to prepare the smear samples which were then used to examine the proliferation of P388 leukemic cells.

The result thereof is represented in FIGS. 10 and 11. As can be seen from FIGS. 10 and 11, the control group (FIG. 10) showed colony formation and continued proliferation of P388 leukemic cells, but group B (FIG. 11), to which the composition(AG60) of the present invention was administered, showed only normal cells rather than P388 leukemic cells.

2) Lifetime extension effects of the composition(AG60) of the present invention in P388 cell-transplanted mice:

To determine the lifetime extension effect of the composition(AG60) of the present invention in mice into which cancer cells are transplanted, 5 mice in each group as survived after the above test 1) were subjected to the same experimental procedure as the above test 1) for 3 days and then the result obtained from group B, to which the present composition(AG60) is administered, was compared with that of control group A.

Figure 12:
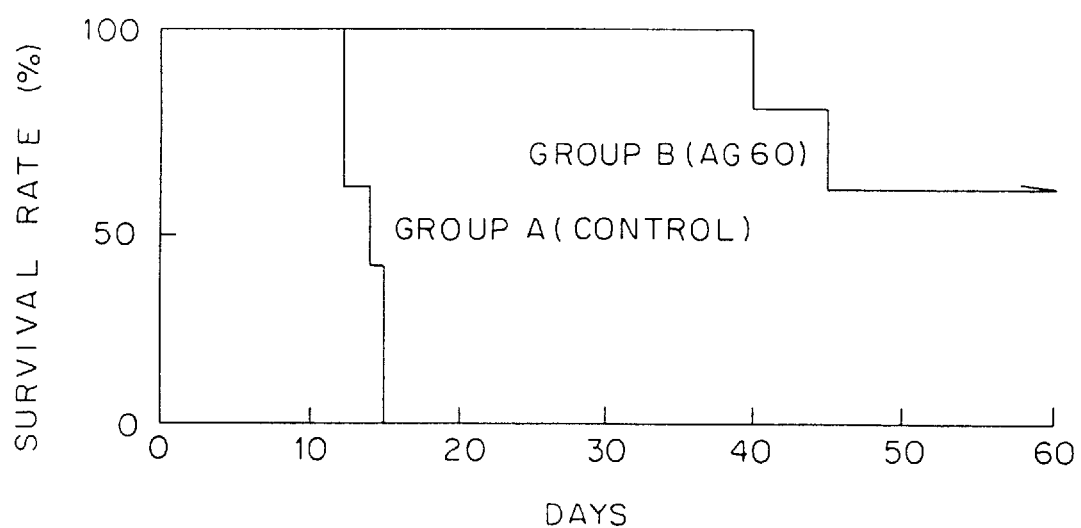
FIG. 12 is a graph showing the lifetime extension effect of the anti-cancer composition(AG60) of the present invention in cancer-transplanted mouse [A: control group, physiological saline 10 ml/kg/i.p., B: the present composition (AG60) 30 mg/kg/i.p.]

The result as observed is presented in FIG. 12. As can be seen from FIG. 12, all mice of control group A died of cancer at 12 to 15 days after transplantation but in group B, to which the present composition(AG60) was administered, 2 mice died at 40 to 45 days after cancer cell transplantation and the remaining 3 mice survived over the observation period(60 days). Thus, the group B showed the lifetime extension effect 2 to 2.5 times that of control group A.

Experiment 7

Anti-cancer effect of the composition(AG60) of the present invention on L1210 leukemia 1) Effect of the composition(AG60) of the present invention on L1210 leukemic cells:

Normal 14 $CDF_1$ mice(♂, 20±1 g) were divided into two groups such that each group included 7 mice. L1210 leukemic cells were transplanted into mouse peritoneum in an amount of $1 \times 10^5$ cells per mouse. After 24 hours from transplantation, control group A received physiological saline in an amount of 10 ml/kg by intraperitoneal injection once a day, for 7 days, and group B received the composition (AG60) of the present invention in an amount of 30 mg/kg in the same manner as control group A. At 2 days after termination of administration, two mice in each group were killed and then subjected to laparotomy. The peritoneal ascitic fluid was plated and then subjected to Giemsa staining to prepare the smear samples which were then used to examine the proliferation of cancer cells.

The result thereof is represented in the FIGS. 13 and 14. As can be seen from FIGS. 13 and 14, control group (FIG. 13) showed a continuous proliferation of P388 leukemic cells but no normal cells were found, and group B (FIG. 14), to which the composition (AG60) of the present invention is administered, showed only normal histiocytes rather than cancer cells.

2) Lifetime extension effect of the composition(AG60) of the present invention in P388 leukemic cell-transplanted mice:

To determine the lifetime extension effect of the composition(AG60) of the present invention in mice into which cancer cells were transplanted, 5 mice in each group as survived after the above test 1) were subjected to the same experimental procedure as the above test 1) for 3 days and then the result obtained from group B, to which the present composition(AG60) was administered, was compared with that of control group A.

Figure 15:
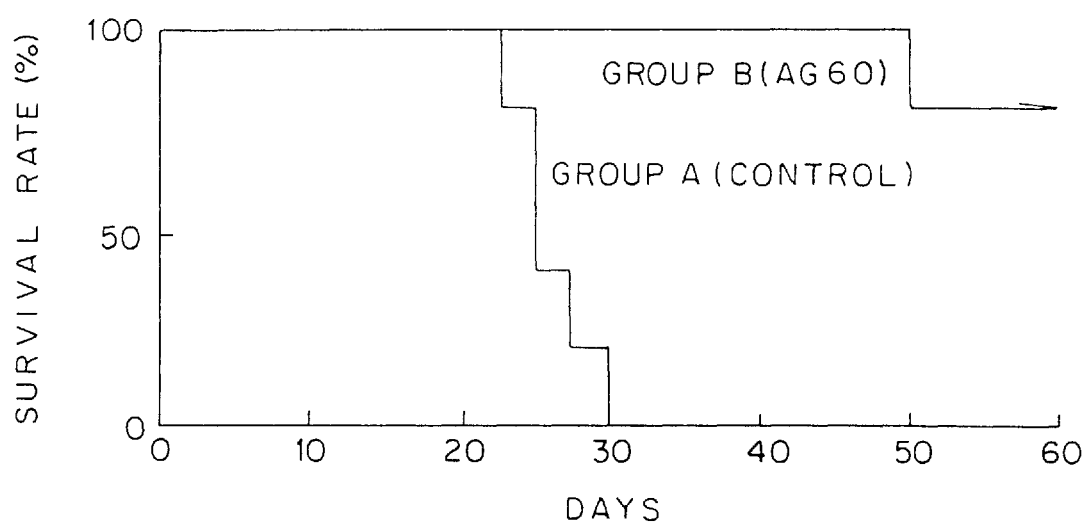
FIG. 15 is a graph showing the lifetime extension effect of the anti-cancer composition(AG60) of the present invention in mice into which L1210 leukemic cells are transplanted [A: control group, physiological saline 10 ml/kg/i.p., B: the present composition(AG60) 30 mg/kg/i.p.]

The result as observed is presented in FIG. 15. As can be seen from FIG. 15, all mice of control group A died of cancer at 26 to 33 days after the cancer cell transplantation but all mice of group B, to which the present composition(AG60) was administered, survived over the observation period(60 days).

Experiment 8

Anti-cancer effect of the composition(AG60) of the present invention on solid tumor Normal 10 ICR mice(♂, 20±2 g) were divided into two groups such that each group included 5 mice. Ehrlich cancer cells were subcutaneously transplanted into mouse inguinal region in an amount of $1 \times 10^7$ cells per mouse. At 24 hours after transplantation, control group A received physiological saline in an amount of 10 ml/kg by intramuscular injection once a day, for 20 days, and group B received the composition(AG60) of the present invention in an amount of 30 mg/kg in the same manner as control group A. In each group, the proliferation pattern of solid tumor was observed from the fifth day after transplantation once every 2 days, and the weight was measured before transplantation or on the sixth day after transplantation. At 21 days after transplantation of cancer cells, all mice in the two groups were killed to remove only the solid tumor tissues. The excised tissue of group B was compared with that of the control group A. The tumor mass(26.3 mm×20 mm) samples were prepared from the excised tissues to conduct the histopathological examinations. Separately, the inguinal lymph nodes(7 mm×5 mm) were removed from the left axillary region and subjected to H&E staining(hematoxylin and eosin staining) to prepare the tissue specimens which were then used to conduct the histopathological examinations.

Figure 16:
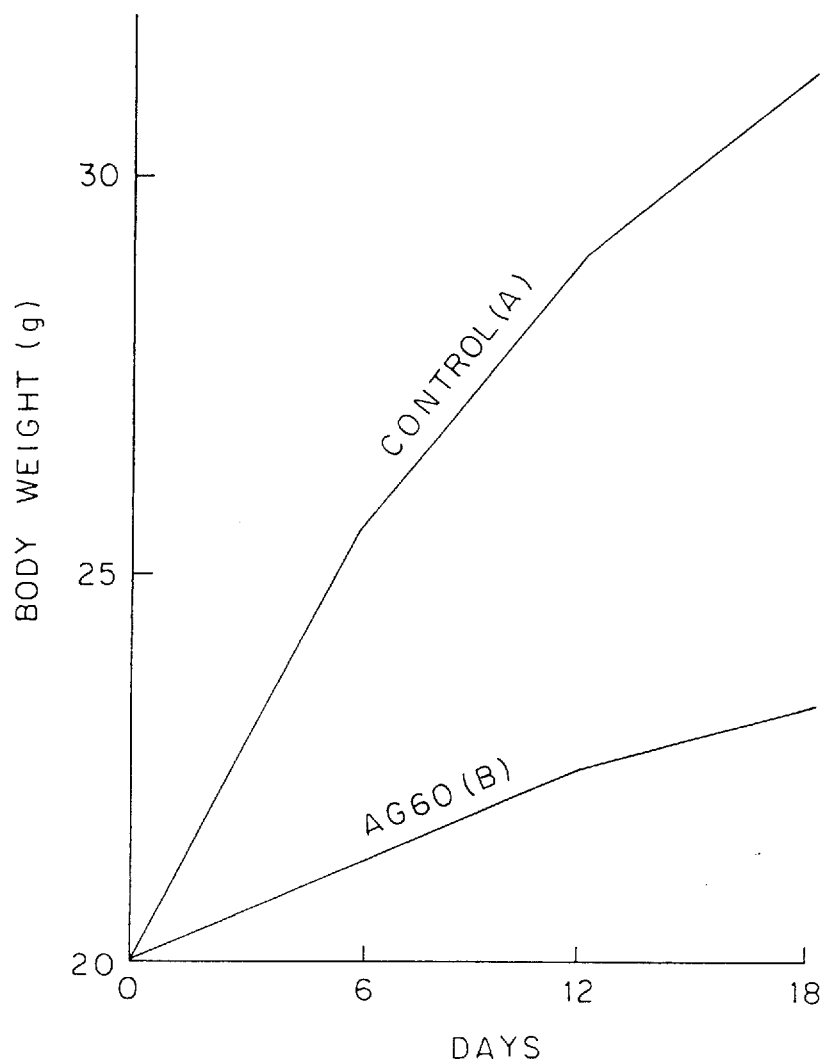
FIG. 16 is a graph showing the effect of the anti-cancer composition(AG60) of the present invention on the body weight of mice into which Ehrlich solid tumor cells are transplanted [A: control group, physiological saline 10 ml/kg/i.m., B: the present composition(AG60) 30 mg/kg/ i.m.]
Figure 17:
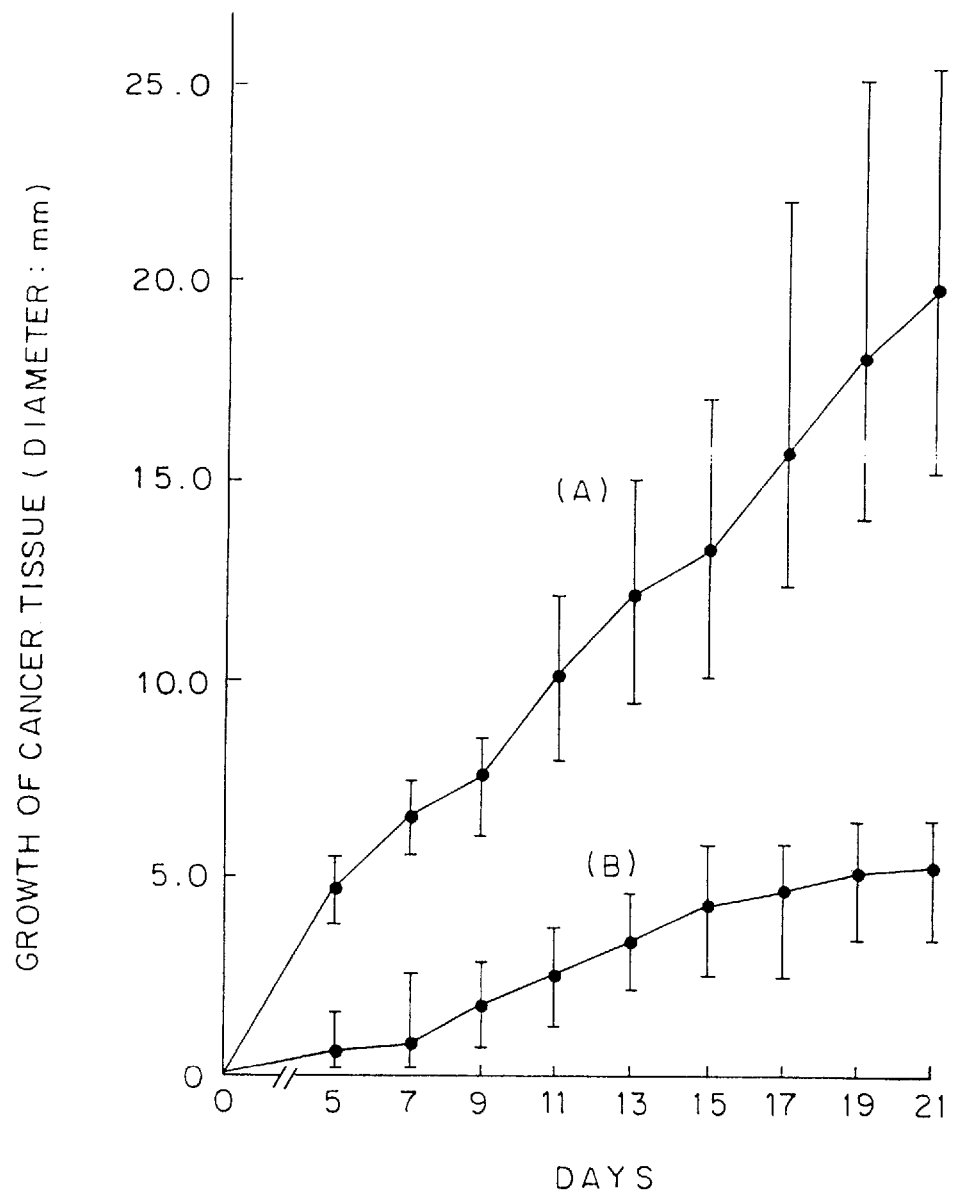
FIG. 17 is a graph showing the inhibitory effect of the anti-cancer composition(AG60) of the present invention against cancer cell proliferation in mice into which Ehrlich solid tumor cells are transplanted [A: control group, physiological saline 10 ml/kg/ i.m., B: the present composition (AG60) 30 mg/kg/i.m.]
Figure 18:
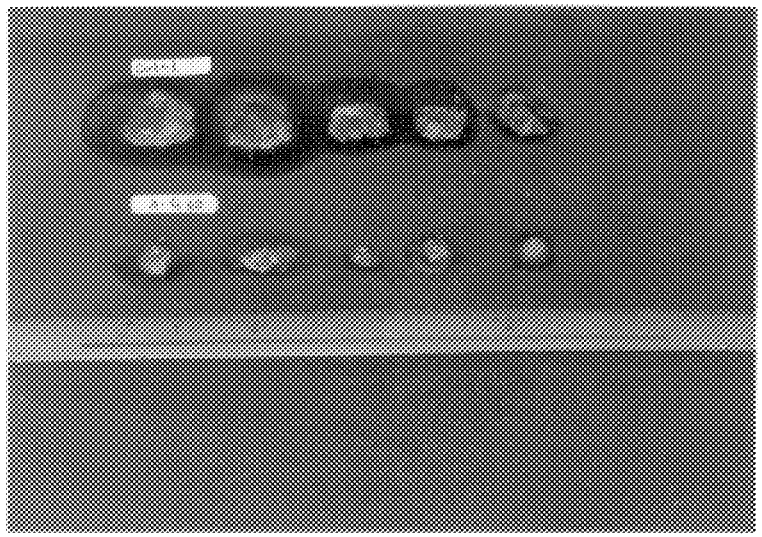
FIG. 18 is photograph showing the inhibitory effect of the anti-cancer composition(AG60) of the present invention against cancer cell proliferation in mice into which Ehrlich solid tumor cells are transplanted [A: control group, physiological saline 10 ml/kg/ i.m., B: the present composition (AG60) 30 mg/kg/i.m.]
Figure 20A:
FIGS. 20A and 20B are photographs of the macroscopic findings of Ehrlich sarcoma tissue, which shows the inhibitory effect of the anti-cancer composition(AG60) of the present invention against cancer proliferation and infiltration in mice into which Ehrlich solid tumor cells are transplanted [A: control group, physiological saline 10 ml/kg/i.m. (←: proliferated tumor cells), B: the present composition(AG60) 30 mg/kg/i.m. (←: proliferated tumor cells)]
Figure 20B:
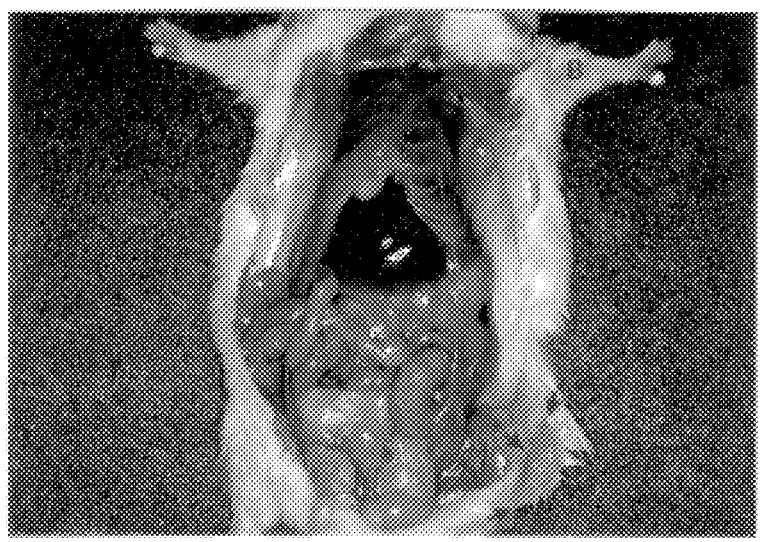
Figure 19:
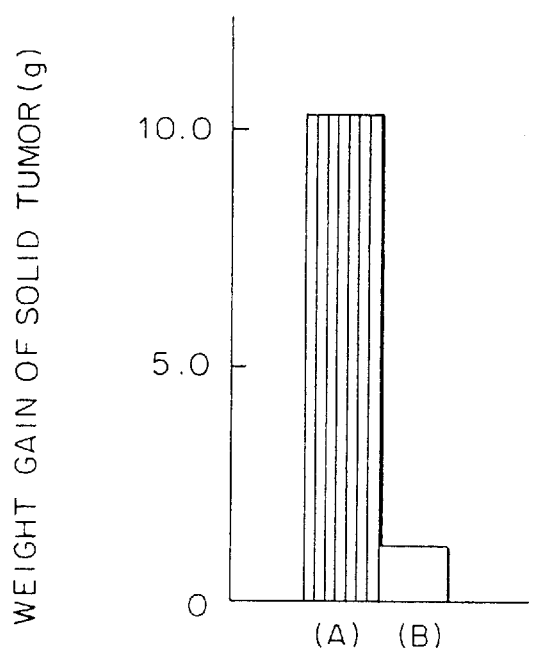
FIG. 19 is a graph showing the tumor weight changes resulting from the inhibitory effect of the anti-cancer composition(AG60) of the present invention against cancer proliferation in mice into which Ehrlich solid tumor cells are transplanted [A: control group, physiological saline 10 ml/kg/i.m., B: the present composition(AG60) 30 mg/kg/ i.m.]
Figure 21A:
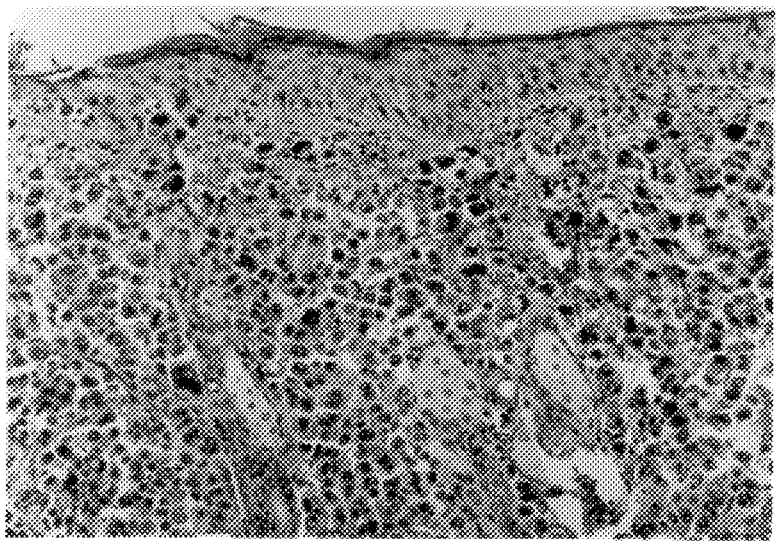
FIGS. 21A, 21B, 21C and 21D are photographs showing the microscopic findings of inguinal tissue in mice into which Ehrlich solid tumor cells are transplanted, as the control group [A: ← replacement of dermis layer with cancer cells (X4), B: ← growth of cancer cells in inguinal region (X4), C: ← growth of cancer cells extended to subcutaneous muscular layer in inguinal region (X4), D: ← cancer tissues in inguinal region (X20)]
Figure 21B:
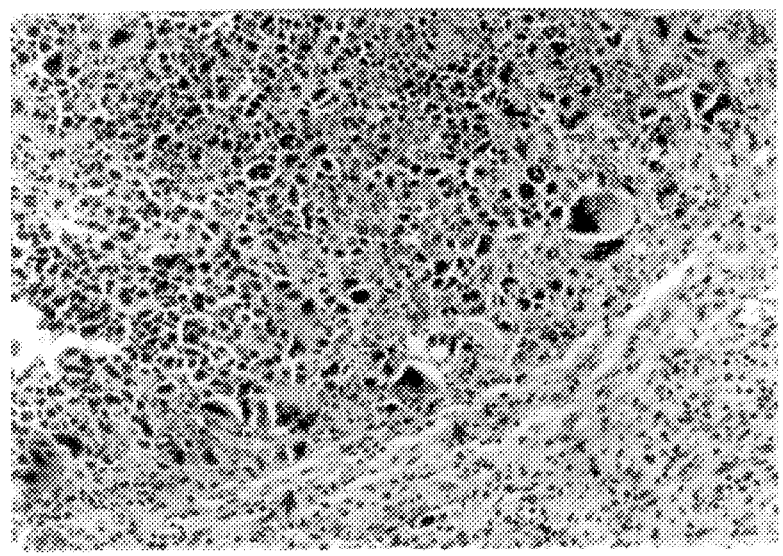
Figure 21C:
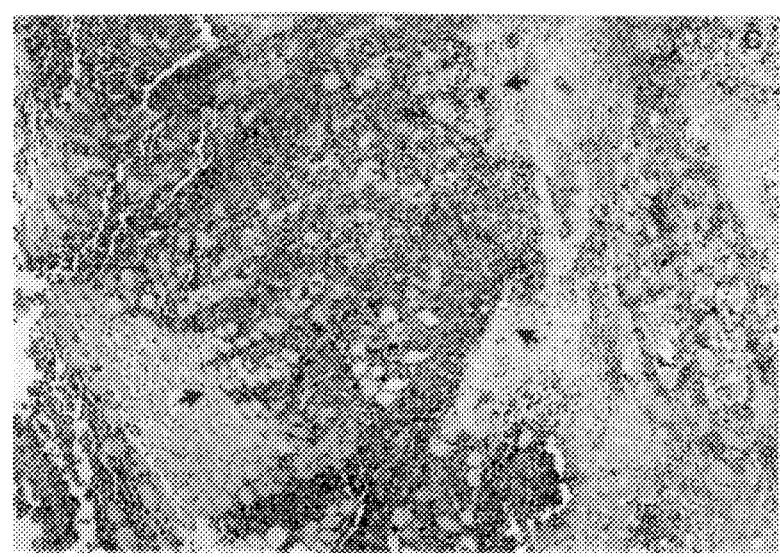
Figure 21D:
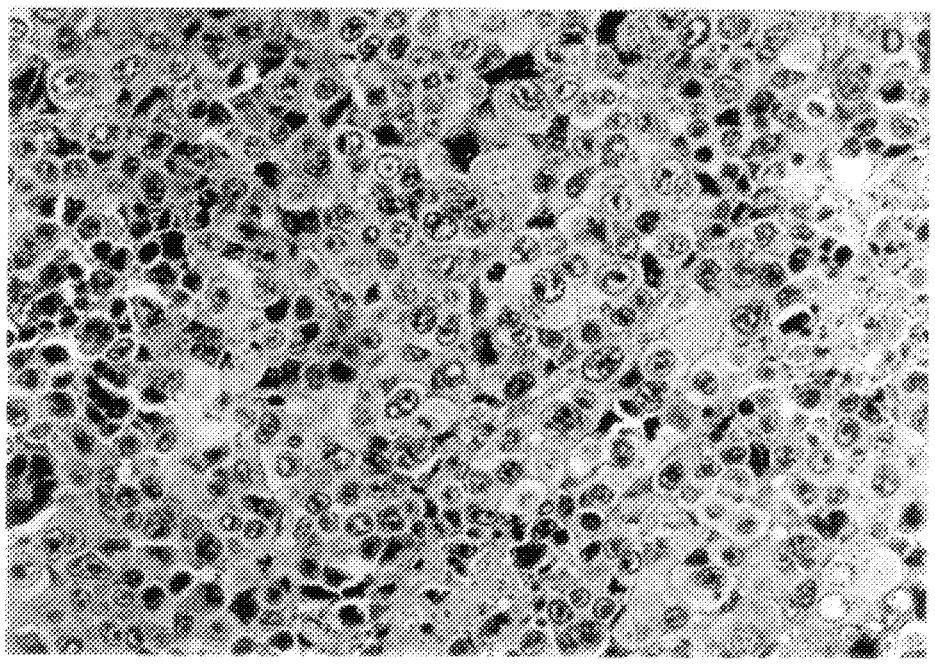
Figure 22A:
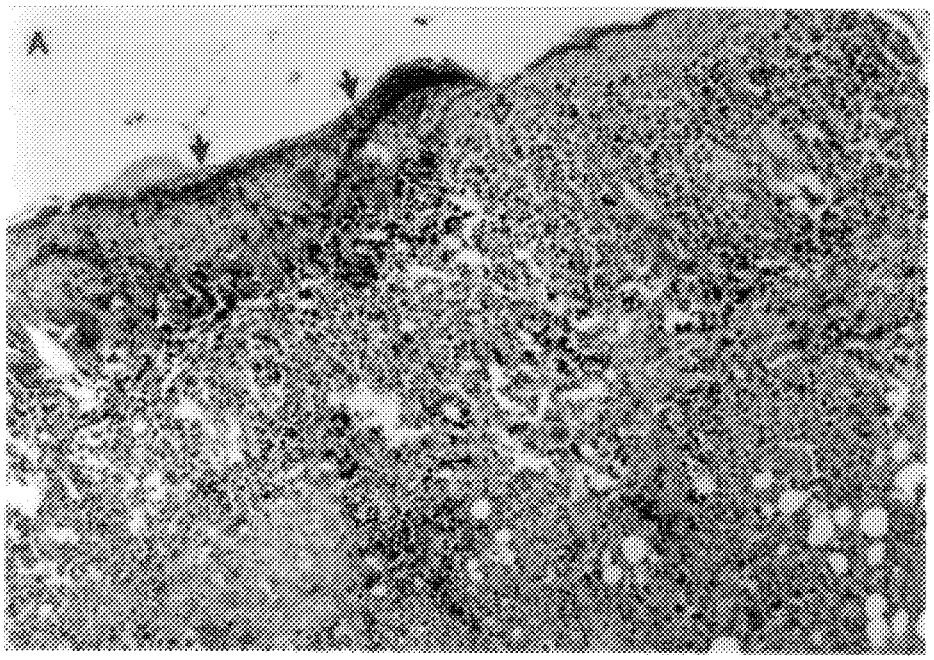
FIGS. 22A, 22B and 22C are photographs showing the inhibition of cancer cell infiltration around inguinal region with the anti-cancer composition(AG60) of the present invention in mouse into which Ehrlich solid tumor cells are transplanted [A: ← necrosis of epithelial layer and upper and middle dermis layer in tumor region, ⇐ replacement with inflammatory cells (X4), B: ← extensive necrosis of dermis layer around tumor mass, ⇐ inflammatory reaction (X4), C: ← progressive necrosis of cancer cells in the central region of tumor mass (X10)]
Figure 22B:
Figure 22C:
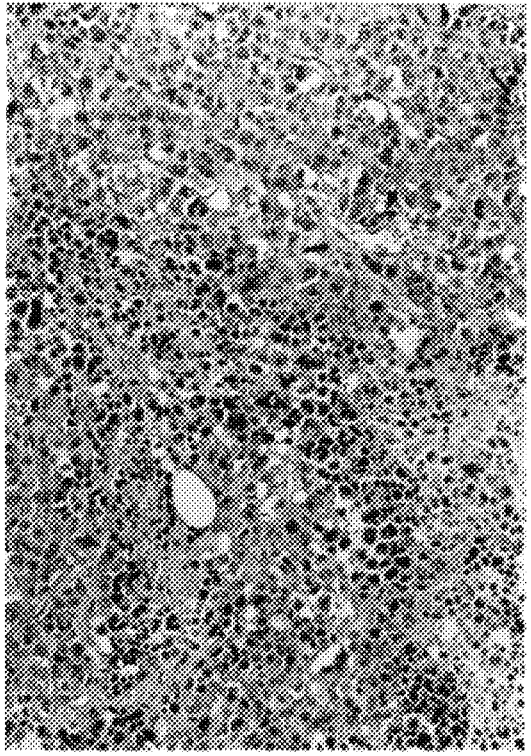
Figure 22D:
FIGS. 22D and 22E are photographs showing the inhibition of cancer cell infiltration around inguinal region with the anti-cancer composition(AG60) of the present invention in mouse into which Ehrlich solid tumor cells are transplanted [D: ← replacement of tumor mass with necrosis zone, ⇐ extensive infiltration of inflammatory cells, E: ← replacement of tumor mass with extensive necrosis zone (X10)]
Figure 22E:

1) The result of body weight measurement is shown in the following Table 5 and FIG. 16. As can be seen from Table 5 and FIG. 16, the weight gain on the eighteenth day after cancer cell transplantation was approximately 12.0 g in the control group A and only approximately 3.3 g in the group B to which the present composition(AG60) was administered. Accordingly, it could be considered that the weight gain was in proportion to the proliferation of cancer tissues. Thus, it is highly likely that the body weight in the control group increased due to a dramatic increase in cancer tissues but in group B, to which the present composition(AG60) was administered, the body weight was slowly gained since the cancer cell proliferation was inhibited by the present composition(AG60).

TABLE 5

Effect of the present composition(AG60) on body weight of solid tumor-transplanted mouse

| Group | Day Weight(g) | | | |
|---|---|---|---|---|
| | 0 | 6 | 12 | 18 |
| A(control group) | 20.2 | 25.5 | 28.9 | 32.2 |
| B(AG60, 30 mg/kg) | 20.1 | 21.2 | 22.3 | 23.1 |

2) The result of examinations of tumor tissue proliferation pattern is presented in FIGS. 17, 18, 19 and 20. As can be seen from FIGS. 17 and 18, the diameter of tumor tissue in control group A was 15–26.5 mm, whereas the diameter of tumor tissue in group B, to which the present composition (AG60) was administered, was merely 3.2–6.2 mm. The result of measurement of tumor weight at 21 days after transplantation is presented in FIG. 19. As can be seen from FIG. 19, the weight gain of tumor tissue in control group A was 11.7 g, whereas in group B, to which the present composition(AG60) was administered, the weight gain of tumor tissue was merely 1.1 g. The result of histopathological examinations is presented in FIG. 20. As can be seen from FIG. 20, in control group A the tumor tissue was continuously proliferated and extended to muscles around inguinal portion, whereas in group B, to which the present composition (AG60) was administered, the proliferation activity of tumor cells was inhibited to reduce the tumor size and the weight of tumor tissue was only one-tenth(1/10) as heavy as that of control group B.

3) The result of the histological examinations of tumor tissue is presented in FIGS. 21, 22A, 22B, 22C, 22D and 22E. As can be seen from FIG. 21, in the control group it could be observed that the epithelial layer was partially necrotized and the infiltration of cancer cells was broadly extended to dermis layer and muscular layer. The cancer cells were mostly in the epithelial layer, having distinct nucleoli and chromatins. Some of the cancer cells were dividing and huge cancer cells were also observed. Around the tumor tissue infiltration of inflammatory cells and necrosis area were partially present, but necrosis in the central part of tumor tissue was not found. In group B to which the present composition(AG60) was administered at the dose of 30 mg/kg (FIGS. 22A and 22D), it was observed that the epithelial layer was diffusely necrotized, inflammatory cells were extensively infiltrated, the tumor tissue was divided into lobules, and necrotic bands were observed between and around the lobules of tumor tissues. Particularly, dead cancer cells were observed, extending from the exterior of living cancer cells to the interior part thereof, the portion in which cancer cells disappeared formed extensive necrotic bands, and infiltration of inflammatory cells, in particular lymphocytes, was generally observed in the borderline between normal dermis layer and the necrotic band.

Figure 23A:
FIGS. 23A and 23B are photographs showing the microscopic examination of lymph nodes in mouse into which Ehrlich solid tumor cells are transplanted, as the control group [A: ← normal lymph follicle, ⇐ reactive proliferation (X4), B: ⇐ reactive proliferation (enlargement of cavity in A (X10))]
Figure 23B:
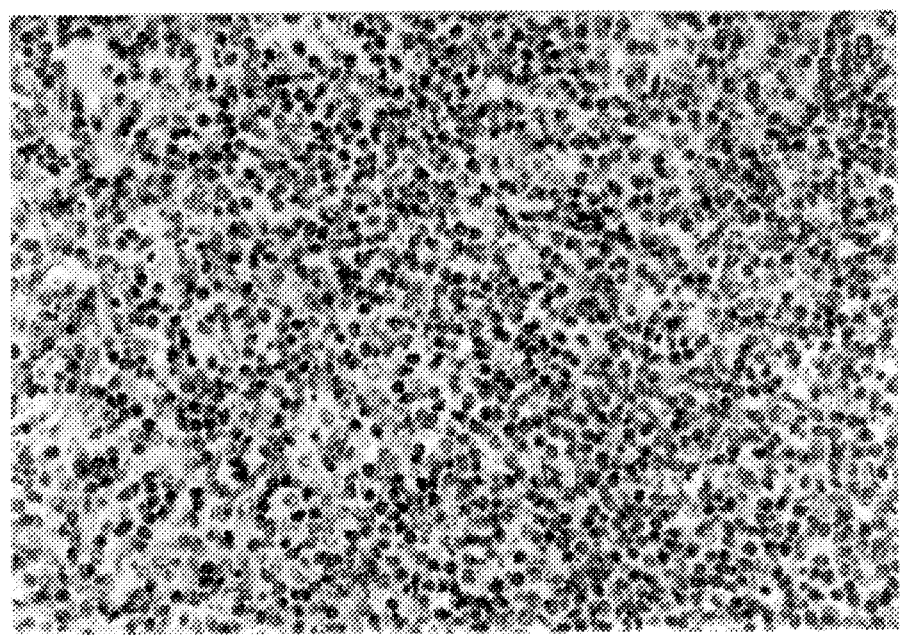
Figure 24A:
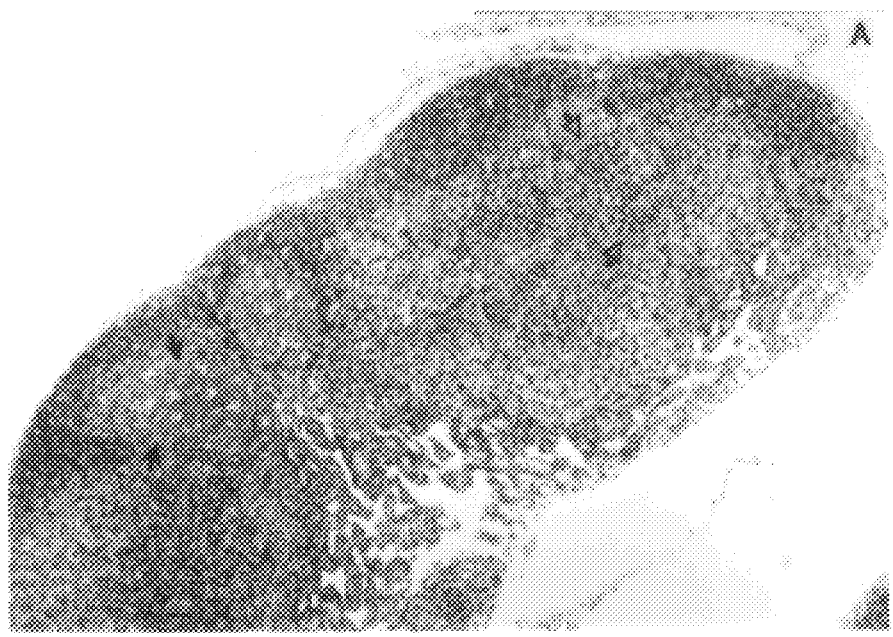
FIGS. 24A and 24B are photographs showing the microscopic examination of lymph nodes in mouse into which Ehrlich solid tumor cells are transplanted and to which the anti-cancer composition(AG60) of the present invention is administered [A: ⇐ reactive hyperproliferation (X4), B: ⇐ reactive hyperplasia (enlargement of cavity in A (X10)].
Figure 24B:
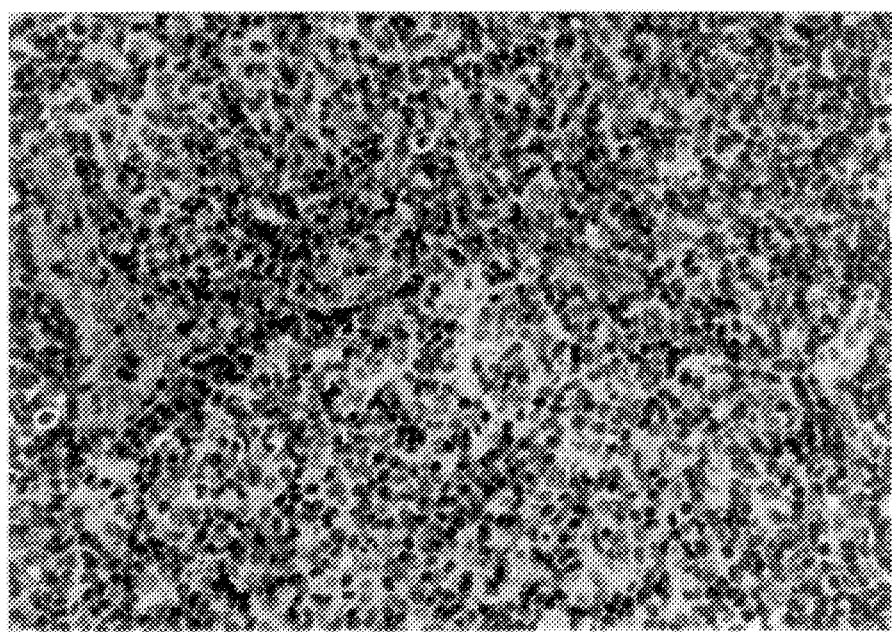

4) The result of the histological examination of lymph node is represented in FIGS. 23 and 24. As can be seen from FIG. 23, in the control group the lymph follicle disappeared and reactive hyperplasia was observed, but metastasis of cancer cells was not observed. In group B, to which the present composition(AG60) was administered, at the dose of 30 mg/kg (FIG. 24), normal lymph follicles and reactive hyperplasis were present partially together, but no metastasis of cancer cells was observed.

As mentioned in the above experiments, the combination of acriflavine neutral and guanosine hydrate which potentiates the effects of acriflavine neutral, i.e. the composition (AG60) according to the present invention, exhibits a reduced toxicity and an increased anti-cancer effect in comparison with the single use of acriflavine neutral or guanosine hydrate. The composition (AG60) according to the present invention as an anti-cancer composition has a high affinity to DNA and inhibits the synthesis of DNA and RNA, and at the same time, causes changes in cellular surface to increase the cell agglutination induced by lectins. In addition, the composition(AG60) according to the present invention disintegrates the nuclear membrane, makes chromosomes loosened and forms irregular debris even in nucleoli to reduce the synthesis of rRNA in cancer cells. However, other theories may also explain the activity observed. Furthermore, it can be supposed that the present composition(AG60) acts competitively with ions such as $Ca^{++}$, $Mg^{++}$, etc., to inhibit the binding of other cations to phospholipids, has an effect on the cellular membrane integrity, and inhibits the ion transport to block the function of cellular membrane, thereby exhibiting the anti-cancer effect of the present composition (AG60).

The composition(AG60) according to the present invention has an aqueous fluorescent coloring property and an affinity to nucleic acids and does not cause any damage to normal cells. In addition, the present composition(AG60) shows a potent antagonistic effect on purine metabolism of malignant tumor to bring changes in purine metabolism mechanism and therefore, inhibits the tumor growth and has the effect of inhibiting or eliminating the cancer cell proliferation.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A composition comprising enhanced anti-tumor effective amounts of an acridine derivative and a guanosine compound, wherein the acridine derivative is selected from the group consisting of acriflavine and acriflavine neutral and the salts and mixtures thereof, and the guanosine compound is selected from the group consisting of guanosine, guanosine hydrate, isoguanosine and the salts and mixtures thereof.

2. The composition of claim 1, wherein the acridine derivative and the guanosine compound are present in the constitutional ratio of 1:0.1–5.0.

3. The composition of claim 2, wherein the acridine derivative is acriflavine neutral and the guanosine compound is guanosine hydrate.

4. The composition of claim 2, wherein the acridine derivative and the guanosine compound are present in the constitutional ratio of 1:0.3–3.0.

5. The composition of claim 4, wherein the acridine derivative is acriflavine neutral and the guanosine compound is guanosine hydrate.

6. The composition of claim 4, wherein the acridine derivative and the guanosine compound are present in the constitutional ratio of 1:0.5–1.5.

7. The composition of claim 6, wherein the acridine derivative is acriflavine neutral and the guanosine compound is guanosine hydrate.

8. The anti-cancer composition of any one of claim 1, wherein the acridine derivative is acriflavine neutral and the guanosine compound is guanosine hydrate.

9. The composition of claim 1, wherein the composition further comprises an enhanced anti-tumor effective amount of an immunomodulator, anti-tumor agent or pharmaceutically acceptable carrier.

10. The composition of claim 9, wherein the immunomodulator and anti-tumor agent is one or more components selected from the group consisting of cisplatin, 5-fluorouracil, tamoxifen, adriamycin, mitomycin, methotrexate, picivanil, lectins, interferones, monoclonal antibodies and human immunoglobulins.

11. A method for treating lung cancer, hepatoma, leukemia, solid tumor and carcinoma originated from epithelial tissue, comprising administering to a patient in need of such treatment an effective amount of the composition of claim 1.

* * * * *